US009238348B2

(12) United States Patent
Zhou et al.

(10) Patent No.: US 9,238,348 B2
(45) Date of Patent: Jan. 19, 2016

(54) METHOD OF MANUFACTURE OF ARTICLE FOR DELIVERING HEALTH-BENEFIT AGENT

(75) Inventors: Peiguang Zhou, Appleton, WI (US); David Gerard Iwanski, Sherwood, WA (US); Gary Alan Turchan, Greenville, WI (US); Stephen David Franger, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 450 days.

(21) Appl. No.: 13/601,147

(22) Filed: Aug. 31, 2012

(65) Prior Publication Data

US 2013/0240139 A1 Sep. 19, 2013

Related U.S. Application Data

(63) Continuation-in-part of application No. 12/856,120, filed on Oct. 8, 2010, now Pat. No. 8,552,251.

(51) Int. Cl.
*B32B 5/16* (2006.01)
*B32B 5/02* (2006.01)
*B32B 5/30* (2006.01)
*B32B 7/12* (2006.01)
*B32B 5/24* (2006.01)
*A61L 15/44* (2006.01)
*A61L 15/46* (2006.01)
(Continued)

(52) U.S. Cl.
CPC .............. *B32B 5/16* (2013.01); *A61F 13/15617* (2013.01); *A61F 13/15658* (2013.01); *A61F 13/15699* (2013.01); *A61L 15/34* (2013.01); *A61L 15/44* (2013.01); *A61L 15/46* (2013.01); *A61L 15/58* (2013.01); *A61L 15/60* (2013.01); *B32B 5/022* (2013.01); *B32B 5/24* (2013.01); *B32B 5/30* (2013.01); *B32B 7/12* (2013.01); *A61F 13/8405* (2013.01)

(58) Field of Classification Search
CPC .............. B32B 5/16; B32B 5/02; B32B 5/30; B32B 7/12; B32B 5/24
USPC ........................................................ 156/276
See application file for complete search history.

(56) References Cited

U.S. PATENT DOCUMENTS 3,919,437 A 11/1975 Brown et al.
4,345,907 A 8/1982 Wegele et al.
(Continued)

FOREIGN PATENT DOCUMENTS

EP 0 172 341 A2 2/1986
EP 0 067 418 B1 9/1986
(Continued)

OTHER PUBLICATIONS

Co-pending U.S. Appl. No. 12/856,120, filed Oct. 8, 2010, by Zhou et al. for "Article With Health-Benefit Agent Delivery System."

*Primary Examiner* — Daniel Lee
(74) *Attorney, Agent, or Firm* — Kimberly-Clark Worldwide, Inc.

(57) ABSTRACT

A laminate of nonwoven materials having fine particulate matter attached thereto is made with a lamination process capable of supplying up to about 60 gsm of particulate matter to a substrate. The particulate matter may be applied to the substrate using a powder coating apparatus. The laminate may be used in personal absorbent articles such as diapers, feminine pads, bandages, bed pads, and the like.

9 Claims, 11 Drawing Sheets

(51) Int. Cl.
*A61L 15/34* (2006.01)
*A61L 15/58* (2006.01)
*A61L 15/60* (2006.01)
*A61F 13/15* (2006.01)
*A61F 13/84* (2006.01)

(56) References Cited

U.S. PATENT DOCUMENTS

| | | | |
|---|---|---|---|
| 4,685,909 | A | 8/1987 | Berg et al. |
| 5,776,839 | A | 7/1998 | Dischler et al. |
| 5,977,430 | A | 11/1999 | Roe et al. |
| 6,017,832 | A | 1/2000 | Yahiaoui et al. |
| 6,120,488 | A | 9/2000 | VanRijswijck et al. |
| 6,120,783 | A | 9/2000 | Roe et al. |
| 6,166,285 | A | 12/2000 | Schulte et al. |
| 6,281,407 | B1 | 8/2001 | Warner et al. |
| 6,503,524 | B1 | 1/2003 | Tyrrell et al. |
| 6,503,525 | B1 | 1/2003 | Paul et al. |
| 6,517,848 | B1 | 2/2003 | Huard et al. |
| 6,534,074 | B2 | 3/2003 | Krzysik et al. |
| 6,551,607 | B1 | 4/2003 | Minerath, III et al. |
| 6,761,711 | B1 | 7/2004 | Fletcher et al. |
| 6,849,303 | B2 | 2/2005 | Dave |
| 6,855,134 | B2 | 2/2005 | Brooks |
| 6,867,287 | B2 | 3/2005 | Carlucci et al. |
| 6,969,378 | B1 | 11/2005 | Vukos et al. |
| 7,608,069 | B2 | 10/2009 | Zehner et al. |
| 7,771,735 | B2 | 8/2010 | Dvoracek et al. |
| 7,879,350 | B2 | 2/2011 | MacDonald et al. |
| 2002/0087129 | A1 | 7/2002 | Di Luccio et al. |
| 2003/0130636 | A1 | 7/2003 | Brock et al. |
| 2003/0135172 | A1* | 7/2003 | Whitmore et al. ............ 604/359 |
| 2005/0096623 | A1* | 5/2005 | Nhan et al. ............... 604/385.22 |
| 2005/0137544 | A1 | 6/2005 | Schroeder et al. |
| 2006/0020250 | A1 | 1/2006 | Chester et al. |
| 2007/0137812 | A1 | 6/2007 | Shannon et al. |
| 2008/0135195 | A1 | 6/2008 | Hermans et al. |
| 2008/0294131 | A1 | 11/2008 | Nonnenmann et al. |
| 2009/0042469 | A1 | 2/2009 | Simpson |
| 2009/0131890 | A1 | 5/2009 | Rourke et al. |
| 2009/0197089 | A1 | 8/2009 | Klippert |
| 2009/0266478 | A1 | 10/2009 | Schafer et al. |
| 2010/0009165 | A1 | 1/2010 | Patel et al. |
| 2010/0239678 | A1 | 9/2010 | Razavi |
| 2012/0089067 | A1 | 4/2012 | Zhou et al. |
| 2012/0165770 | A1 | 6/2012 | Zhou et al. |

FOREIGN PATENT DOCUMENTS

| | | |
|---|---|---|
| EP | 0 462 680 B1 | 10/1996 |
| EP | 1 118 343 A1 | 7/2001 |
| JP | 2007-039775 A | 2/2007 |
| WO | WO 92/15404 A1 | 9/1992 |
| WO | WO 99/06078 A1 | 2/1999 |
| WO | WO 00/69483 A1 | 11/2000 |
| WO | WO 01/49933 A2 | 7/2001 |
| WO | WO 03/004070 A1 | 1/2003 |
| WO | WO 2004/080358 A1 | 9/2004 |
| WO | WO 2005/044163 A1 | 5/2005 |
| WO | WO 2005/123750 A1 | 12/2005 |
| WO | WO 2006/034830 A1 | 4/2006 |
| WO | WO 2008/054268 A1 | 5/2008 |

* cited by examiner

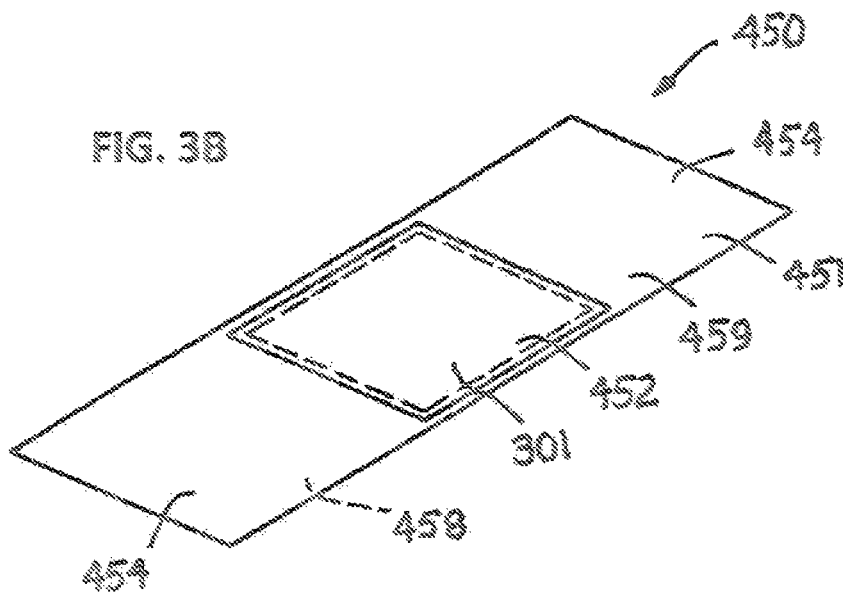
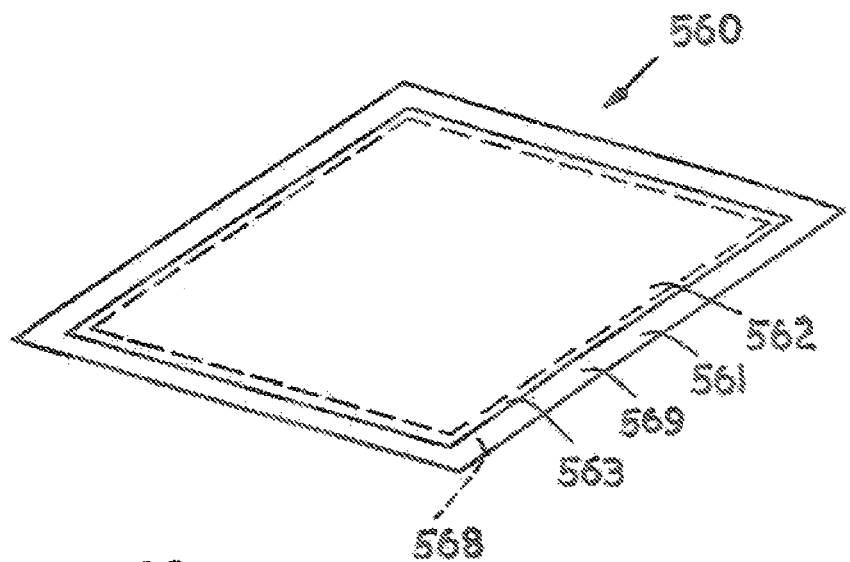

METHOD OF MANUFACTURE OF ARTICLE FOR DELIVERING HEALTH-BENEFIT AGENT

This application claims priority as a continuation-in-part of application Ser. No. 12/856,120, filed on Oct. 8, 2010 now U.S. Pat. No. 8,552,251. The entirety of application Ser. No. 12/856,120 is incorporated herein by reference.

This disclosure relates to the manufacture of an article in the form of a laminate constructed with nonwoven and/or film substrates, to which one or more layers of particulate matter is attached thereto.

BACKGROUND OF THE DISCLOSURE

Certain personal or health articles, regardless of whether they are absorbent, can develop undesirable odors or even skin irritation. For example, a diaper with urine absorbed into the diaper's absorbent member can create an environment that is moist relative to an unused diaper. This moisture can provide an environment conducive to bacterial growth. Bacteria residing on the skin can create odor and irritation. The same problem is associated with disposable articles such as adult incontinence pads/underwear, menstrual pads, bed pads, bandages, sweat bands and the like. Really, any situation where a nonwoven or film is used against wetted or moist skin has the potential problem of creating odor, discomfort, bacterial overgrowth and/or skin irritation.

To alleviate this problem, health-benefit agents such as lotions, powders, particulates or other substances have been applied to the outermost body-facing surface of the liner material that has direct contact with the skin including mucus membranes. While somewhat effective, when the lotion or powders and/or particulates are wetted, they can flow to non-beneficial areas on the article. For instance, a diaper may have lotion applied to the crotch region of a diaper. When wetted, the lotion can flow away from the crotch region to sections that are not in direct contact with the skin or intimate areas that could benefit from the health-benefit agent.

As such, there is a need for an article that can provide a health-benefit agent to a person when it is in direct or even indirect bodily contact. Such benefits include reduction or eradication of: odor, bacteria, viruses, discomfort, irritation, wet sensation, and/or the like. There is also a need for an article that can be used to apply a health benefit agent to the skin or other intimate areas of the body, be it a natural supplement or a drug. Further, it is desired that the solution to the problems noted above is desirably cost efficient as compared to current single layer nonwovens or films used to make absorbent articles. Desirably, the article will not require a change in the manufacturing processes where it is used, such as the processes for making absorbent articles such as diapers etc.

SUMMARY OF THE DISCLOSURE

The present invention is a directed to a method for constructing a laminate that includes the following steps: fluidizing an amount of particulate matter, wherein the particulate matter is selected from a group consisting of menthol, activated charcoal, carbon, silica gel, xylitol, clay, dessicants, prebiotics, probiotics, surfactants, anti-oxidants, disinfectants, antibacterial agents, antiviral agents, pharmaceutical actives, perfumes, deodorants, opacifiers, astringents, preservatives, superabsorbent material and a combination thereof; creating a base by (1) conveying at a speed of 30 to 600 meters/minute a first substrate and a second substrate, each having an inner surface and an outer surface, (2) attaching a first adhesive layer to the inner surface of the first substrate, and (3) applying an amount of the fluidized particulate matter onto the first adhesive layer to create a first layer of particulate matter; and creating a cover by attaching a second adhesive layer to the inner surface of the second substrate. The base is attached to the cover so that the outer surfaces of the first substrate and the second substrate are exposed.

In another aspect of the invention, a method for constructing a nonwoven laminate includes the steps of: fluidizing an amount of particulate matter; conveying a first nonwoven substrate and a second nonwoven substrate; attaching a first adhesive layer to an inner surface of the first nonwoven substrate; electrostatically attaching a first layer of particulate matter to the first adhesive layer at a rate of 8-40 gsm, the particulate matter having a particle size of 2-120 microns; attaching a second adhesive layer to an inner surface of the second nonwoven substrate; and attaching the second adhesive layer to the first layer of particulate matter.

Other features and aspects of the present invention are discussed in greater detail below.

BRIEF DESCRIPTION OF DRAWINGS

A full and enabling disclosure of the present invention, including the best mode thereof to one of ordinary skill in the art, is set forth more particularly in the remainder of the specification, including reference to the accompanying figures in which:

FIG. 3B is a bandage having one embodiment of a liner of the present invention.

FIG. 3C is a bed pad having one embodiment of a liner of the present invention.

Figure 1:
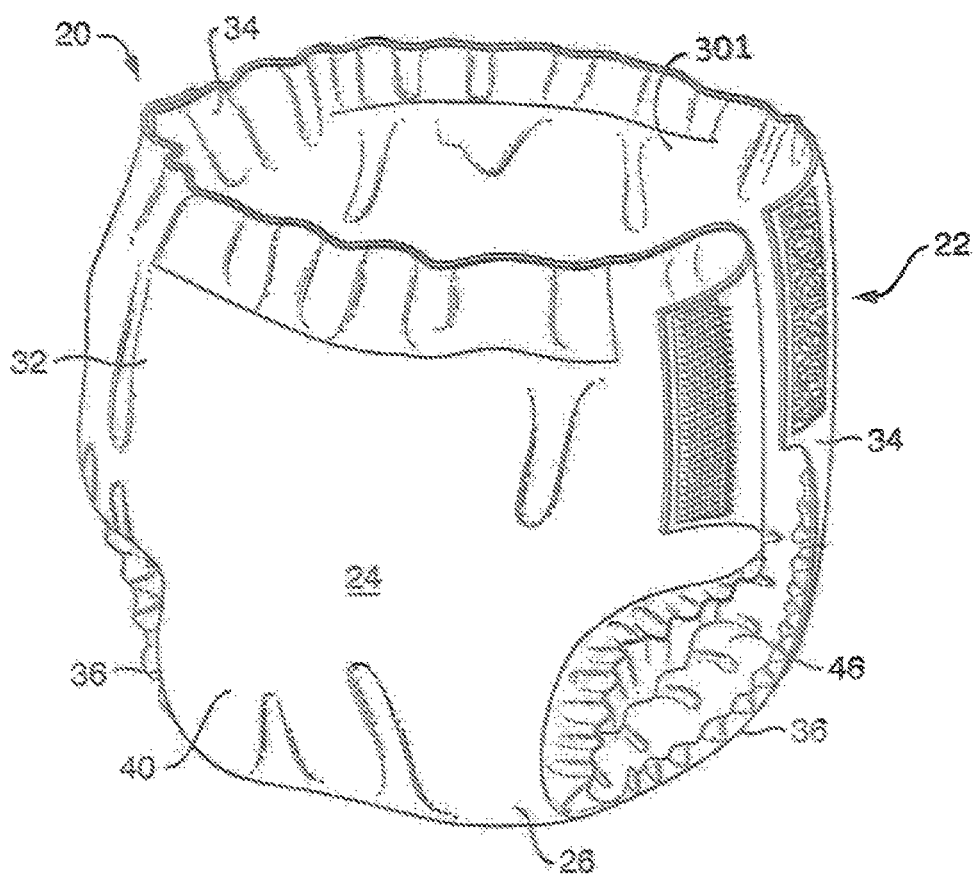
FIG. 1 representatively illustrates a front view of a training pant in a fastened state, showing a liner according to one embodiment of the present invention.

Repeated use of reference characters in the present specification and drawings is intended to represent the same or analogous features or elements of the present invention. Not all analogous features are referenced by repeat reference characters. The drawings are representational and are not necessarily drawn to scale. Certain proportions thereof may be exaggerated, while others may be minimized.

DEFINITIONS

Adhesive Bond

The term "adhesive composition" or "adhesive" as used herein generally refers to a substance that bonds two faces of one or more substrates together. The term "bond" refers to the adhering of two elements. Two elements will be considered to be bonded together when they are bonded directly or indirectly to one another.

Adhesive Bonding Process

The term "adhesive bonding" means a process which forms a bond by application of an adhesive. The application of adhesive composition may be by various processes such as slot coating, spray coating and other topical applications. To form a health benefit layer, the adhesive composition may be mixed with a product component such as one or more health benefit agents and/or adhesives. Pressure may be applied to the health benefit layer so that it can be joined to other layers of laminate.

Attached

The term "attached" as used herein means that there is direct contact between a layer X and a layer Y or between layer X and another material with no other material located between such layers unless specified, such as when an adhesive is used.

Film

As used herein, the term "film" refers to a thermoplastic film made using a film extrusion and/or other forming process, such as a cast film or blown film extrusion process. The term includes apertured films, slit films, and other porous or microporous films which constitute liquid/vapor/air transfer films, as well as barrier films which do not transfer liquid.

Hot Melt Adhesive

Conventional hot-melt adhesive is an adhesive composition that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. A typical hot-melt adhesive composition might contain from about 15 to about 35 weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive compositions comprising different weight percentages of these components are possible.

Laminate

As used herein the term "laminate" refers to a composite structure of two or more layers that have been joined to each other with an attachment or bonding step, such as through adhesive bonding, thermal bonding, point bonding, pressure bonding, extrusion coating or ultrasonic bonding.

Layer

The term layer, when used in the singular, is a single element of composite structure such as the laminate/liner of the present invention.

Liner

Liners are commonly used in personal care articles such as diapers, feminine pads, incontinence garments and the like. Thus, the term "liner" describes a material that directly faces and makes contact with the skin. A liner according to the present invention is a material having a laminate structure.

Nonwoven

A class of fabrics produced by attaching fibers (e.g. such as by chemical or mechanical means), or both. The nonwoven fabric is made by mechanical, chemical, thermal, or solvent means, or with an adhesive, or any combination of these, and is distinct from woven, knitted or tufted materials. Nonwoven fabrics may be made from synthetic thermoplastic polymers or natural polymers such as cellulose. For example, cellulosic tissue is one type of a nonwoven material.

Particles

Particles refer to any geometric form, such as, but not limited to, spherical grains, crystalline shapes, cylindrical fibers or strands, and the like. Particle sizes are defined infra.

Pores

As used herein, the term "pores" refers to apertures, either naturally occurring or man made in a substrate material. A slit is considered a pore in the context of the present invention.

Prebiotic

The prebiotic definition is not limited to a specific bacterial group. Generally, prebiotics are non-digestible ingredients that beneficially affect the host by selectively stimulating the growth and/or activity of one or a limited number of generally beneficial bacteria. Prebiotics are defined as dietary fibers, and can include but are not limited to fructooligosaccharides, inulin, transgalactosylated oligosaccharides, and soybean oligosaccharides.

Probiotics

Certain live microorganisms, which when administered in adequate amounts, can confer a health-benefit on a host. Lactic acid bacteria and bifidobacteria are the most common types of microbes used as probiotics; but certain yeasts and bacilli may also confer a health benefit. For example, by using probiotics, health effects regarding urogenital infections and atopic diseases may cease or be mitigated.

Melt Blowing

A nonwoven web forming process that extrudes and draws molten polymer resins with heated, high velocity air to form fine filaments. The filaments are cooled and collected as a web onto a moving screen. The process is similar to the spunbond process, but meltblown fibers are much finer and generally measured in microns.

Spunbond

A technology in which the filaments have been extruded, drawn and laid on a moving screen to form a web. The term "spunbond" is often interchanged with "spunlaid," but the industry has conventionally adopted the spunbond or spunbonded term to denote a specific web forming process. This is to differentiate this web forming process from the other two forms of the spunlaid web forming, which are meltblown and flashspinning methods.

Spunbond/Meltblown Composite

This laminar composite (laminate) is a multiple-layer fabric that is generally made of various alternating layers of spunbond ("S") and meltblown ("M") webs: SMS, SMMS, SSMMS, etc. (or ABA, ABBA, AABBA etc.).

Substrate

A substrate is typically a web that in the context of present invention, is a nonwoven material or film to which an adhesive and health-benefit agent may be attached.

Tissue

As used herein, a "tissue product" generally refers to various paper products, such as facial tissue, bath tissue, paper towels, sanitary napkins, and the like. A tissue product of the present invention can generally be produced from a cellulosic web having one or multiple layers. For example, in one embodiment, the tissue product can be defined by a single-layered cellulosic web formed from a blend of fibers. In another embodiment, the tissue product can be defined by a multi-layered paper (i.e., stratified) web. Furthermore, the paper product can also be a single- or multiply product (e.g., more than one cellulosic web), wherein one or more of the plies may contain a cellulosic web formed according to the present invention. Normally, the basis weight of a tissue product of the present invention is less than about 120 grams per square meter (gsm), in some embodiments less than about 70 grams per square meter, and in some embodiments, between about 10 to about 40 gsm. One reference is U.S. Pat. No. 6,893,537 issued on May 17, 2005, is incorporated herein in a manner that is consistent therewith.

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It is to be understood by one of ordinary skill in the art that the present discussion is a description of exemplary embodiments only, and is not intended as limiting the broader aspects of the present disclosure.

DETAILED DESCRIPTION OF THE DISCLOSURE

The consumer products industry has known for years that certain parts of the body (e.g. skin) may be somewhat affected when an article is placed against the body for the management of bodily fluids and excretions, wounds, infection control and the like. For example, the age-old problem of diaper rash or malodors. The present invention can solve the problem for various disposable absorbent articles, including but not limited to, personal care absorbent articles, health/medical absorbent articles, sports/construction absorbent articles, and the like, without departing from the scope of the present invention.

Figure 2:
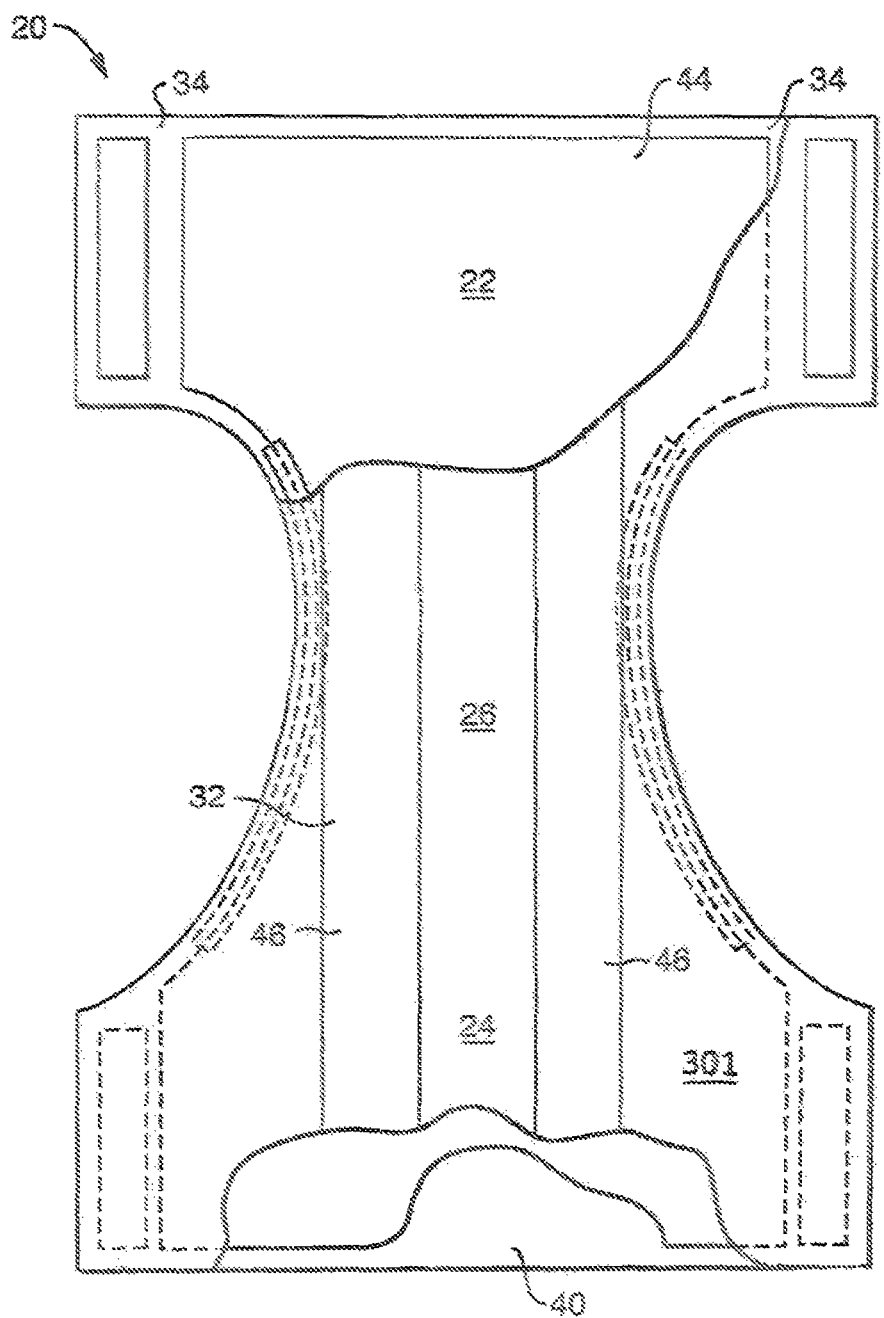
FIG. 2 representatively illustrates a plan view of the training pant of FIG. 1 in an unfastened, stretched and laid flat condition, showing the surface of the training pant that faces toward the wearer which is the liner of the present invention.

In general, the present disclosure can be generally described as a health-benefit-agent delivery system for the skin and other areas of the body. To gain a better understanding of the present invention, attention is directed to FIGS. 1 and 2 showing just one exemplary article that can be made with the laminate or "liner" of present invention. Specifically, a training pant is shown and described.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

FIG. 1 illustrates a training pant 20 in a partially fastened condition, and FIG. 2 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges and a pair of longitudinally opposite waist edges.

The illustrated pant 20 may include a chassis 32, and a pair of laterally opposite front side panels 34 extending laterally outward at the front region 22.

The chassis 32 includes a backsheet 40 and a liner 301 (a laminate of the present invention) that may be joined to the backsheet 40 in a superimposed relation therewith by adhesives, ultrasonic bonds, thermal bonds or other conventional techniques. The chassis 32 may further include an absorbent core 44 such as shown in FIG. 2, the absorbent core disposed between the backsheet 40 and the liner 301 for absorbing fluid body exudates exuded by the wearer. The absorbent core may further include a pair of containment flaps 46 secured to the liner 301 or the absorbent core 44 for inhibiting the lateral flow of body exudates.

The backsheet 40, the liner 301 and the absorbent core 44 may be made from many different materials known to those skilled in the art. All three layers, for instance, may be extensible and/or elastically extensible.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomer, as well as combinations thereof.

In this particular article, the liner 301 is used to prevent the absorbent core from touching the user's skin. The liner 301 is also sufficiently liquid permeable to permit liquid body exudates to penetrate through its thickness to the absorbent core 44.

The liner 301 may be extensible and/or elastomerically extensible. Suitable elastomeric materials for construction of the liner 301 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomer, HYTREL elastomer, ESTANE elastomeric polyurethanes (available from Noveon, a business having offices located in Cleveland, Ohio U.S.A.), or PEBAX elastomer. The liner 301 can also be made from extensible materials such as those described in U.S. Pat. No. 6,552,245 to Roessler et al. which is incorporated herein by reference in a manner that is consistent herewith. The liner 301 can also be made with biaxially stretchable materials as described in U.S. Pat. No. 6,969,378 to Vukos et al. which is incorporated herein by reference in a manner that is consistent herewith.

The article 20 can optionally further include a surge management layer (not shown) which may be located between the liner 301 and the absorbent core 44. Using an adhesive or the like, the surge layer may be attached or connected to various components in the article 20 such as the absorbent core 44. For the sake of this invention, the surge layer is considered a part of the absorbent core 44. The surge management layer can temporarily store the liquid prior to releasing it into the storage or retention portions of the absorbent core 44. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The absorbent core 44 can be formed using methods known in the art. While not being limited to the specific method of manufacture, the absorbent core can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith.

In some desirable aspects, the absorbent core 44 includes cellulose fiber and/or synthetic fiber, such as meltblown fiber, for example. Thus, in some aspects, a meltblown process can be utilized, such as to form the absorbent core in a coform line. In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film.

The absorbent core 44 can additionally or alternatively include absorbent and/or superabsorbent material. Accordingly, the absorbent core 44 can comprise a quantity of superabsorbent material and optional fluff contained within a matrix of fibers.

It should be understood that the absorbent core 44 is not restricted to use with superabsorbent material and the optional fluff. In some aspects, the absorbent core 44 may further include materials that are synergized by the health-benefit agents in the liner such as surfactants, ion exchange resin particles, moisturizers, emollients, perfumes, fluid modifiers, odor control additives, and the like, and combinations thereof. In addition, the absorbent core 44 can include foam.

Other very similar applications to the training pant include diapers and incontinence pants.

Generally, it is most desirable that the liner 301, which is in contact with the skin be able to deliver one or more health-benefits. Specifically, the liner 301 operates as a delivery vehicle or reservoir in which various health-benefit agents can be preloaded. The liner 301, which usually makes direct contact with the skin, is capable of releasing health-benefit agents in a controllable way.

Multiple health-benefits can be developed by particle/powder stabilization using a lamination and/or extrusion process. Release kinetics of the health-benefit agents can be controlled by changing the substrates (tissue, non-woven, film) or liner configuration (ABA, AB, ABC etc.) to obtain a desired laminate structure.

Figure 5:
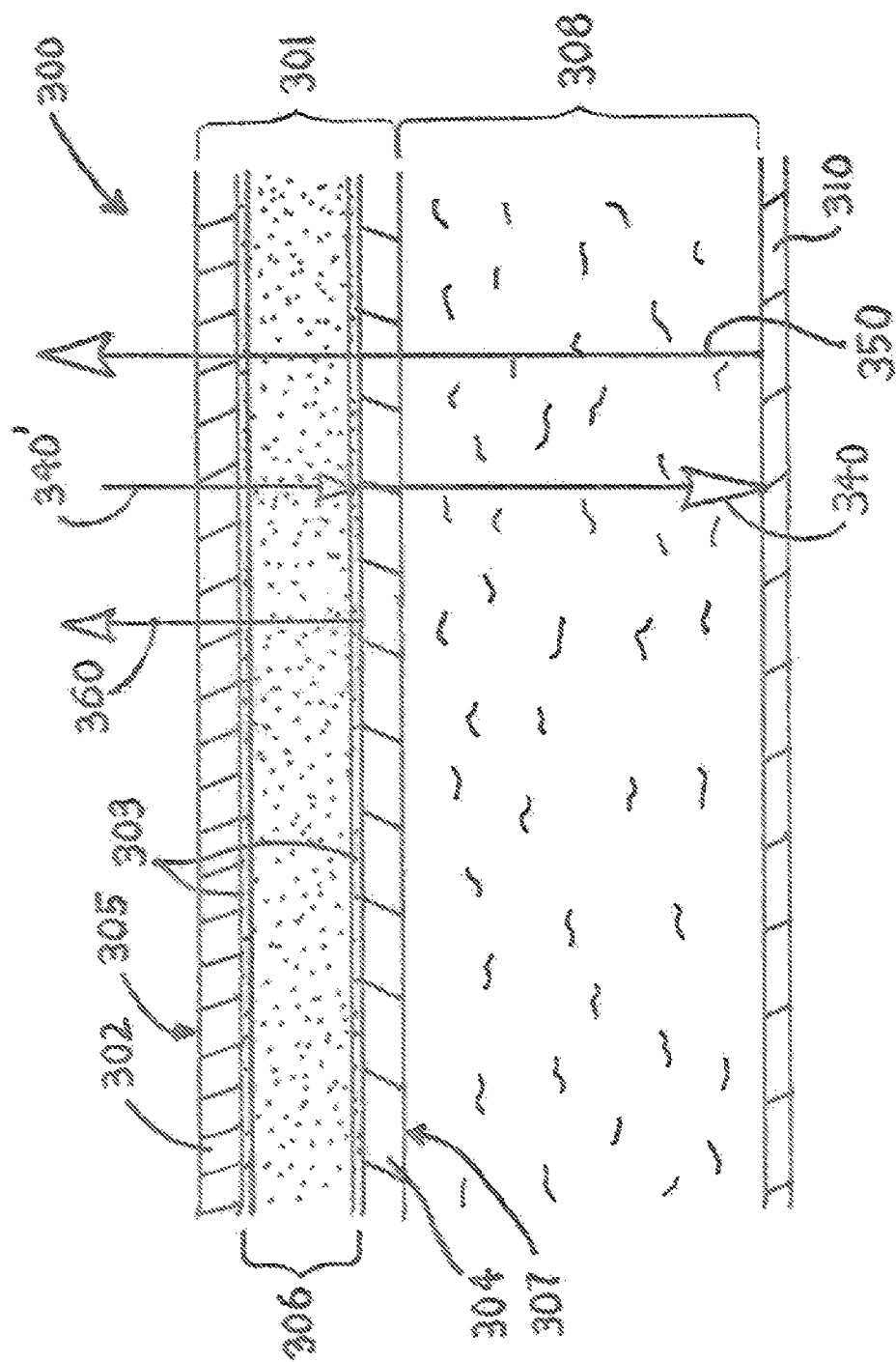
FIG. 5 is a cross-sectional view of one embodiment of a laminate of the present invention, wherein the laminate has three layers.

In the embodiment shown in FIG. 5, there is a simple cross-sectional view of an absorbent article 300 that includes a liner 301, an absorbent core 308 (supra), and a backsheet 310 (supra). This illustration shows the adhesive layers 303. For simplicity, FIGS. 6, 7, 9 and 11 do not actually show the adhesive layers adjacent to the substrates 302 and 304.

The liner 301 is a three-layer structure made from an exposed substrate 302, an inner substrate 304 and a health-benefit layer 306 located therebetween. Substrate 302 may be made from a nonwoven (desirably tissue) or a film material if these materials have pores that allow liquid to transfer therethrough. In a desired embodiment, components 302 and 304 may be defined by a cellulosic tissue web. This tissue web may be single-ply and have about a 10-20 gsm basis weight. In another embodiment, it is desirable that the tissue web has about a 16 gsm basis weight. The tissue web may be white or any other desired color. One possible source of tissue webs is CelluTissue, Natural Dam, N.Y.

Still referring to FIG. 5, inner substrate 304 may either have the same material characteristics as does substrate 302. For example, suppose substrates 302, 304 and health-benefit layer 306 are represented by layers A, B, and C respectively. Each designation A, B and C may be different; substrates A and B may be a nonwoven (e.g. tissue) or film. Layer C is a health benefit layer. The following configurations of these elements are possible: ACB, ACA, BCB, BCA, ACBCB etc. For example, ACA is a structure having two identical substrates that are associated with one layer of health benefit layer C. Substrates A and B of liner 301 can be made from film (F), tissue (T), spunbond (SB), spunbond/meltblown/spunbond (SMS) and the like.

Figure 6:
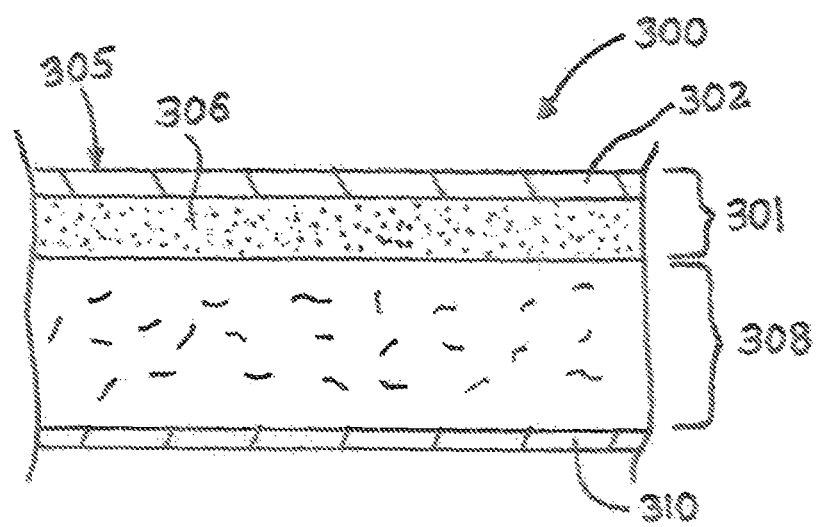
FIG. 6 is a cross-sectional view of another embodiment of a laminate of the present invention wherein the laminate has two layers.

Referring now to FIG. 6, in another embodiment of the present invention, there is no inner substrate 304 seen in the previous embodiment of liner 301. Instead, the health-benefit layer 306 is may be bonded to the absorbent core 308 that may include compositions intended to react with health benefit layer 306 when the absorbent core is wetted. The fabrication of this liner 301 is likely to be made in line with the fabrication of the absorbent article 301.

Figure 11:
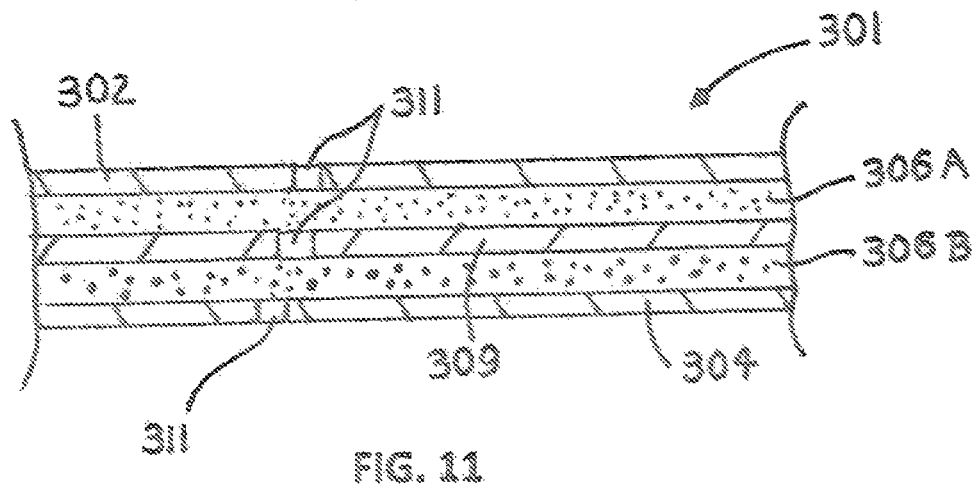
FIG. 11 is a top perspective view of an absorbent body including a patch of laminate according to the present invention.

Referring now to FIG. 11, liner 301 is shown. Liner 301 is made with more than two substrates and more than one health benefit agent layer. In this example, there are three substrates of nonwoven or film materials, layers 302, 309, and 304. There are also two layers of health benefit agent, layers 306A and 306B. As with the prior embodiment, each substrate 302, 309, and 304 may have the same or different characteristics. Liner 301 may have layers A, B, and D makes up the following combinations: ACACA, BCBCB, ACACD, BCBCD, and the like (for brevity, not all combinations are listed). Layers "C" may contain the same or different health benefit materials. Layers C, if different, may react with one another once liner 301 is wetted. This construction is most suitable for different reagents that need to remain completely separate until liquid penetrates the substrate 309. Possibly, the reaction between layer 306A and 306B will together, create the health-benefit agent.

Figure 7:
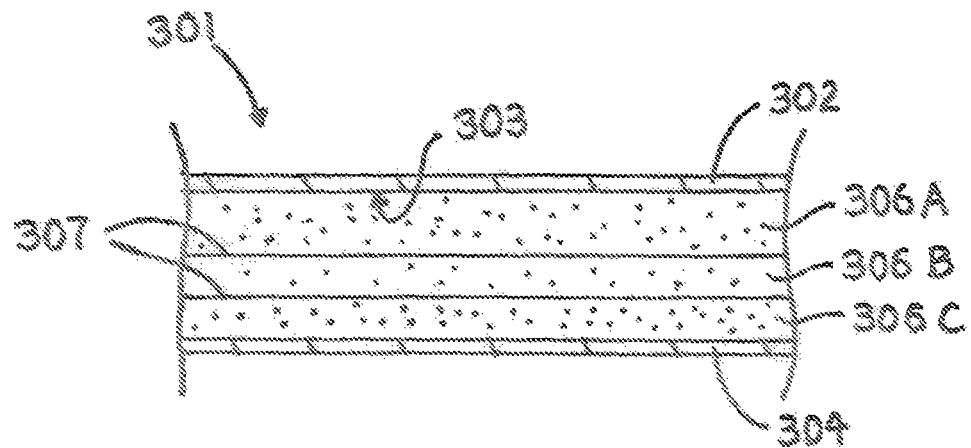
FIG. 7 is a cross-sectional view of another embodiment of a laminate of the present invention, wherein the laminate has three health benefit layers divided by layers of adhesive.

Referring now to FIG. 7, shown is a liner 301 having two substrates (302, 304) made from nonwoven or film materials. As in the prior embodiments of the present invention, substrates 302 and 304 may be made from the same or different nonwoven or films having the same or different characteristics. Between the two substrates 302 and 304, there are three health benefit layers 306A, 306B, and 306C separated by adhesive layers 307. Additional adhesive layers are located at reference 303, but not actually shown to keep the illustration simplistic. Each of the layers 306A, 306B, and 306C may be made from different materials that will remain separated until they come into contact with a liquid such as urine. The layers 306A, B and C may also be separated by the adhesive layers to provide structural stability to the liner. The penetration of liquid from layer 306A to 306C can cause the layers to react with each other to form a health-benefit agent.

Refer back to FIG. 5. In operation, when the liner 301 of the present invention is moistened or wetted, particles or possibly the solute of the health-benefit agent from layer 306 can be released through the exposed substrate 302, thereby imparting a health benefit to the user. For instance, as shown by arrow 340, some fluid will penetrate liner 301 and go into the absorbent core 308. Some fluid will not pass through the inner substrate 304 as indicated by arrow 340. It is sometimes desirable that the bodily exudates flow through the inner substrate 304 in a lower rate as compared to the exterior substrate 302. This allows the majority of active agents to return to the wearer's skin as opposed going directly through the absorbent core 308 (see arrow 360). Regardless, as arrow 350 indicates, fluids coming from the absorbent core 308 or from the interior of the health benefit layer 306 deliver health benefit agents to the user. Pressure from sitting or some other activities is largely responsible for the fluid flow designated by arrows 350 and 360.

Substrate 304 may have pores 311 such that they provide a controlled release of fluid to the absorbent core. In one embodiment, the number and/or size of pores 311 in inner substrate 304 is less than that in substrate 302. This configuration allows the health benefit agents to flow more freely to the user's skin and intimate areas. The pores 311 are only depicted in FIG. 11 so as to prevent the other figures from being overly complex. (The pores 311 are not drawn to scale with respect to other elements of the illustration such as the particles located between the substrates.) As can be seen, the pores 311 may be misaligned with respect to one another, or aligned with one another (not shown). In addition, the pores 311 may vary in size. For instance, the pores 311 in substrate 304 may be smaller that the pores in layers 302 and 309. Many configurations are possible. Likely, the pore 311 configuration we depend on the desired release of health benefit agent to a user.

In another embodiment of the present invention, the liner 301 is prepared according to FIG. 5. Here, compositions such as a drying agent (silica gel or other desiccant), a bacteriostatic/deodorant (xylitol) and superabsorbent particles (SAM) were mixed together and bonded or attached to substrates 302 and 304 to prepare a liner 301. This particular liner 301 has multiple functions such as water absorption, bacteriostatic activity and odor neutralization.

The thickness of layers 302 and 304 may be determined by the Thickness Test as disclosed herein. Desirably, each substrate 302 and 304 will have thickness range of about 0.01 mm to about 0.2 mm; or about 0.025 to about 0.1 mm. Generally, if the laminate is used as a liner in a diaper or other absorbent articles, the thickness of the overall liner will likely not exceed 1 mm as a thickness greater than that may be too bulky for that particular use. Thickness will generally vary because of the variable amount of particulate matter disposed between exposed substrate 302 and inner substrate 304.

Referring to FIG. 5, the health-benefit agent layer 306 is a combination of particulate matter (e.g. prebiotic particles) and adhesive layers 303, as depicted and described herein. It is most desirable to have an adhesive content of about 3 percent to about 10 percent of the total weight of the health-benefit layer 306, or 5 percent to about 10 percent of the total weight of the health-benefit layer 306. This relatively small amount of adhesive leaves much of the particulate matter loose and therefore not completely immobilized by the adhesive. This structure provides the benefit of allowing the health-benefit agent to easily dissolve when wetted, and allowing the resulting liquid to flow through substrates 302 and 304.

A health-benefit agent, singularly or in combination with other health-benefit agents, includes but is not limited to activated charcoal, lactic acid, prebiotics, freeze-dried probiotics, surfactants, anti-oxidants, disinfectants, antibacterial agents, antiviral agents, pharmaceutical actives, perfumes, pigments, deodorants, opacifiers, astringents, solvents, preservatives, and the like. Such agents can deliver an array of consumer health-benefits for odor control, humidity control, pH control, and vaginal health as well as substances that can reduce skin irritation caused by biological insults like feces/urine.

In the present invention, prebiotics serve to increase the number and/or activity of bacteria that are beneficial to the host. In particular, prebiotics are short chain carbohydrates that can be metabolized by probiotics such as *Lactobacillus*. Examples of prebiotics include polysaccharides such as inulin, oligosaccharides such as oligofructose and/or galactooligosaccharides.

Normal vaginal flora is composed of different strains of bacteria. For example, vaginal microflora that consists predominately of *Lactobacillus* species is generally associated with a healthy or normal state. *Lactobacillus* produces lactic acid to lower the pH, hydrogen peroxide, and bacteriocins which make the environment less favorable for pathogenic organisms.

If a wearer of an absorbent article has not changed the article often enough, an imbalance in the vaginal microflora can happen because the bacterial species other than *Lactobacillus* become predominate. An imbalance in vaginal microflora can lead to infection. Administering prebiotics to the labia could help balance the microflora in the vagina by providing a nutrient source for beneficial bacteria that will overtake the harmful bacteria. The same benefit may be seen for the urethra as well. In addition, administration of prebiotic nutrients to the labia can help maintain and stabilize a healthy vaginal microflora by supporting colonization of beneficial bacteria.

A most desired prebiotic for use in absorbent articles is oligofructose. Oligofructose is able to be fermented by a beneficial *Lactobacillus* species. Higher amounts of *Lactobacillus* species within vaginal micro-flora can help prevent bacterial or viral infection. The product application of this prebiotic may include feminine pads and incontinence products such as diapers, pads or pants. It is envisioned that due to its high solubility in water that the prebiotic (e.g. oligofructose) will dissolve in the presence of aqueous solutions and, as a result, have access to the user's skin.

Harmful bacteria such as *Escherichia coli* (*E-coli*) cannot metabolize prebiotics. As a result, the *E-coli* can be outcompeted by beneficial bacteria that can utilize the prebiotics as a food source, and potentially inhibit bacterial infection. Thus, prebiotics may be beneficial to those persons using absorbent products designed to contain feces. The prebiotic will prevent or at least mitigate the spread of *Escherichia coli* in the absorbent products and on the user's skin. Absorbent products include disposable diapers, training pants and incontinence pants.

In all embodiments of liner 301, it is desirable that the health-benefit layer 306 of the present invention include adhesive and appropriate fillers such as desiccants, prebiotics and the like. For example, it may be desirable to use desiccant filler such as silica gel to prevent the prebiotic materials from prematurely absorbing liquid/moisture. Keeping the prebiotic dry will result in an increased product shelf-life. (The silica gel may be available from a source such as Multisorb Technologies, Buffalo, N.Y.)

In another embodiment of the present invention, insoluble, but dispersible hydrophilic compounds can have the ability to sequester fecal irritants. These compounds may also have the ability to absorb water in a diaper environment, thereby removing excess fluid away from skin. Further, these hydrophilic compounds can neutralize odors. A most desirable compound with an odor neutralizing characteristic is clay. It is desirable to use a synthetic clay such as laponite available from Southern Clay Products Inc., Texas. This particular clay has a relatively high water-binding capacity and is light in color which is more desirable for personal care products (a dark clay would make a liner rather dingy and give users the impression that the product is not sanitary).

In another embodiment of the present invention, it is anticipated that volatile odiferous particulates will pass through the substrate 302 and come in contact with one or more health-benefit agents located in layer 306. One example of a health benefit agent is an odor neutralizing compound (e.g. activated charcoal, carbon or the like).

In a further embodiment it is anticipated that urine components such as ammonia may pass through the outer substrate and come in contact with neutralizing agents (e.g., organic acids such as lactic acid). It is envisioned that due to the neutralizing agent's high solubility in water, that it would dissolve in the presence of water/urine and then have access to skin.

Another skin benefit agent is xylitol. Xylitol provides a bacteriostatic/deodorant effect. Another health-benefit presented by xylitol, is that it or certain other sugars in an adequate amount may have a cooling effect when in contact with an aqueous solution or the like. See U.S. patent application Ser. No. 12/646,763 filed on Dec. 23, 2009, incorporated herein to the extent that it is consistent with the present invention.

Skin benefit agents may also reside on the outer surface 305 of exposed substrate 302. However, it should be in mind that some skin benefit agents located on the outer surface 305 may occlude the substrate 302 thereby preventing the beneficial agents located in health benefit layer 306 from surfacing to the outermost surface of the liner 301. Thus, it may be desirable to dispose non-occlusive materials such as aloe and/or water-soluble compounds that include both lactic acid and selective antioxidants like Vitamin C on the surface 303A of substrate 302.

Generally, the process by which the liner 301 is made will determine the overall particle size range. (Particle sizes are measured by the Particle Size Test described herein.) Most embodiments of the present invention will employ particulate health-benefit agents having a particle size from about 10 nm to about 1000 microns. (A nanometer equals 1 billionth of a meter, therefore 1000 nanometers equals 1 micron, while 100 nm equals 0.1 micron.) In one embodiment, the particle size will be about 0.5 to about 5 microns: this is the size range of probiotics. Yet another embodiment of the present invention will have a particle size of about 0.5 microns to about 1000 microns. In a further embodiment of the present invention it will be about 0.5 microns to about 500 microns. Finally, in another embodiment of the present invention, the particle size will be about 100 microns to about 1000 microns. As can be derived, different health-benefit materials require different size ranges.

In one aspect, a health-benefit layer 306 can have a particle-size distribution of between 10 microns and 800 microns, or between 100 microns and 300 microns. In another aspect, the health benefit layer 306 can have a particle size distribution of greater 500 and 710 microns. In another aspect, the health benefit agent layer 306 can have a particle size distribution of less than 500 microns, such as between 50 microns and 500 microns. It should be understood that in aspects where the health benefit agent is in the form of particles, the invention is not limited to the exemplary health benefit agent particle sizes presented above, but rather can include particles having sizes ranging from less than 90 microns (including nanoparticles) to greater than 710 microns.

Desirably, the health benefit layer 306 is strong enough to maintain the integrity of liner 301 when the laminate is substantially dry and worn by a user. In some aspects, health benefit layer 306 has sufficient strength to generally maintain the integrity of the liner 301 when the composite is insulted with an aqueous liquid such as urine or blood.

Desirably, liner 301 is easy to flex. It is desired that the modulus of elasticity should not be more than 125% as compared to current liner materials (e.g. tissue or spunbond having about 16 to 17 gsm).

Referring to FIG. 5, in addition to the exposed substrate 302 and the health benefit layer 306, the liner 301 may include a combination of particles bound with an adhesive 303. The purpose of an adhesive is to help to partially secure the particles (e.g. prebiotic materials) within the health benefit layer 306, and to generally hold the laminate together to form a laminated structure such as liner 301. Desirably, there is a desired amount of adhesive 303, between about 5% and about 10% by weight of the health benefit layer 306. In still other aspects, the total amount of adhesive 303 in the health benefit agent layer 306 can be about 2-10 wt % of the total weight of the health benefit layer 306. Note that the adhesive layer varies in thickness and is not as uniformly applied as shown.

In one embodiment, the health-benefit layer 306 is made with one or more adhesives that transition from a molten state to a solid state. In some aspects, the thermoplastic adhesive composition is suitably a hot-melt adhesive. Such an adhesive generally comprises one or more polymers, such as aliphatic polyolefins, in particular, poly ethylene-co-propylene, polyamides, polyesters, and/or polyether blends; ethylene vinyl acetate copolymers; styrene-butadiene or styrene-isoprene block copolymers; and the like.

As an example, the thermoplastic adhesive may contain from about 15 to about 50 weight percent cohesive strength polymer or polymers; from about 30 to about 65 weight percent resin or other tackifier or tackifiers; from more than zero to about 30 weight percent plasticizer or other viscosity modifier; and optionally less than about 1 weight percent stabilizer or other additive. It should be understood that it is possible to use other hot-melt adhesive formulations comprising different weight percentages of these components. It is also contemplated that the adhesive composition may either be hydrophilic or hydrophobic without departing from the scope of this invention.

Examples of suitable adhesive materials include hydrophobic and hydrophilic hot melt polymers, such as those available from National Starch and Chemical Co. (having a place of business located in Bridgewater, N.J., U.S.A.) such as 34-5610, 34-447A, 70-3998 and 33-2058; those available from Bostik-Findley (having a place of business located in Milwaukee, Wis., U.S.A.) such as HX 4207-01, HX 2773-01, H2525A, H2800; and those available from H. B. Fuller Adhesives (having a place of business located in Saint Paul, Minn., U.S.A.) such as HL8151-XZP. Other adhesives are further described in U.S. Patent Publication No. 2005/0096623 to Sawyer, et al., which is incorporated herein by reference in a manner that is consistent herewith.

It is also contemplated that alternative adhesives may be used without departing from the scope of this invention. Examples of alternative adhesives include polyethylene oxide (PEO); polyethylene glycol (PEG); polyviny alcohol (PVOH); starch derivatives such as starch ethers, carboxymethyl starch, cationic starch, hydroxyalkyl starch, and the like, for example hydroxyethyl starch, hydroxypropyl starch and hydroxybutyl starch; cellulose derivatives such as cellulose ethers, hydroxyalkyl cellulose, for example hydroxyethyl cellulose, hydroxypropyl cellulose, methylcellulose, methyl propyl cellulose, carboxymethyl cellulose, and the like; polyacrylic acid; polyvinylmethyl ether; carrageenan; water-soluble alkyd resins; or the like, ethylene vinyl acetate copolymer (EVA) and combinations thereof. In addition, thermoplastic adhesive fibers, such as thermoplastic binder fibers, can also be used. In other aspects, it may be desirable that the thermoplastic adhesive in layers 306 is water-soluble.

One characteristic of the health benefit layer 306 is basis weight. Accordingly, the basis weight of health benefit layer 306 can range from about 1 gsm to about 100 gsm, such as about 5 gsm to about 50 gsm.

In some aspects, it may be desirable to use a layer 306 that is liquid permeable. However, in cases where the layer 306 is not liquid permeable, the layer can be made permeable by creating pores in the liner 301. Means for perforating materials are well-known in the art, and include, but are not limited to, needle-punch, air-jet, and the like.

Figure 3A:
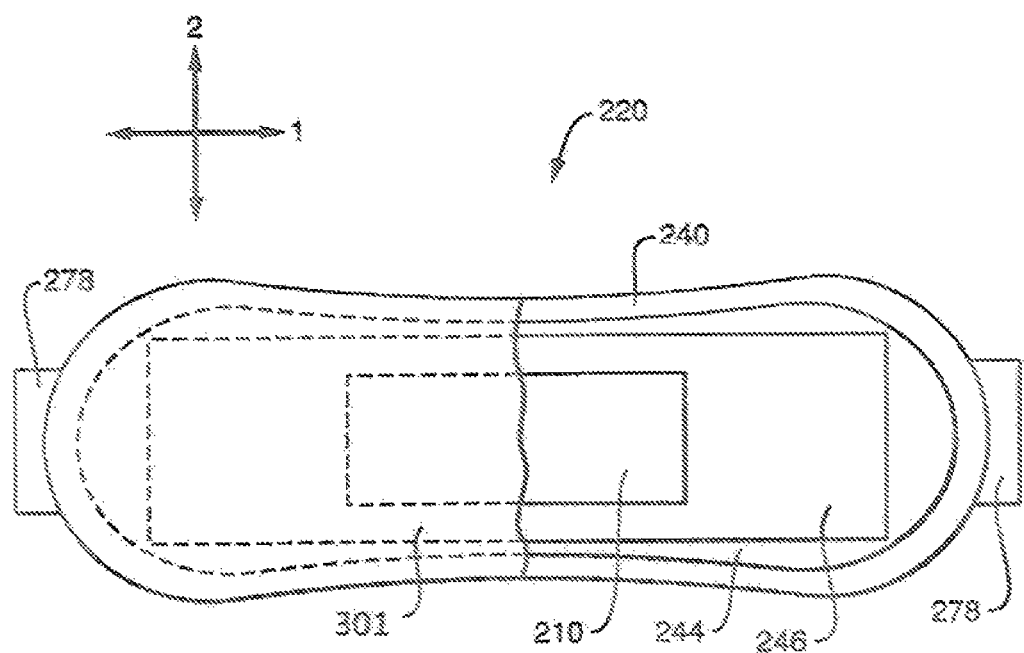
FIG. 3A is a feminine care pad having one embodiment of a liner of the present invention.

While a training pant has been described above for exemplary purposes, it is understood that the composite of the present invention can be suitable for other personal care absorbent articles. For example, FIG. 5 shows a generic cross-section of an absorbent article in that could be part of a feminine-care pad (FIG. 3A), a bed pad (FIG. 3B), and a bandage (FIG. 3C). Of course, the configuration of liner 301 shown in FIG. 5 is not meant to be limiting. Other configurations are seen in FIGS. 6, 7, 9 and 11. There are many other configurations that can be made, but only a select few are shown for sake of brevity.

Example

Menstrual Pads

Referring to FIG. 3A, it is understood that the liner of the present invention can be suitable for feminine pads. For example, shown is an absorbent article 220 in the form of a feminine care pad having a liner 301, a backsheet 240, an absorbent core 244, a surge layer 246, and a peel strip 278. Health-benefit agents applicable to this embodiment of the invention may include but not be limited to vaginal health agents, urethra health agents and skin/mucous membrane health agents. Health-benefits may suppress the growth of yeast, and prevent vaginal or urethral infections by inhibiting colonization of certain bacteria from areas near the vaginal or urethra entrance.

Example

Bandage

In addition to the absorbent menstrual pad and training pant described above, one aspect of the present invention is an absorbent bandage 450. Attention is directed to FIG. 3B which shows one possible configuration for a bandage of the present invention. This is a perspective view of the bandage of the present invention with some of the optional or removable layers not being shown. The absorbent bandage 450 has a strip 451 of material having a body-facing side 459 and a second side 458 which is opposite the body-facing side. The strip 451 essentially operates like a backsheet. The strip 451 may be a material with "pores," such as an apertured film, or material which is otherwise gas permeable, such as a gas permeable film. The strip 451 supports an absorbent core 452 made with absorbent fibers. The absorbent core 456 is attached to the body facing side 459 of the strip. A liner 301 is bonded or attached to the absorbent core 452.

Example

Bed Pad

Absorbent furniture and/or bed pads are also included within the scope of the present invention. As is shown in FIG. 3C, a furniture or bed pad 560 (hereinafter referred to as a "pad") is shown in perspective. The pad 560 has a fluid impermeable backsheet 561 having a furniture-facing side or surface 568 and an upward facing side or surface 569 which is opposite the furniture-facing side or surface 568. The fluid impermeable backsheet 561 supports the absorbent core 563 which comprises superabsorbent material and absorbent fibers of the present invention, and which is attached to the liner 562 of the fluid impermeable backsheet. In addition, liner 562 is applied to the absorbent core. To hold the pad in place, the furniture-facing side 568 of the pad may contain a pressure sensitive adhesive, a high friction coating or other suitable material which will aid in keeping the pad in place during use.

Manufacture

The health benefit layer 306 can be applied to exposed substrate 302 and inner substrate 304 by means well-known in the art. Exemplary means include, but are not limited to melt-blowing, spraying, slot-coating and the like.

Figure 8:
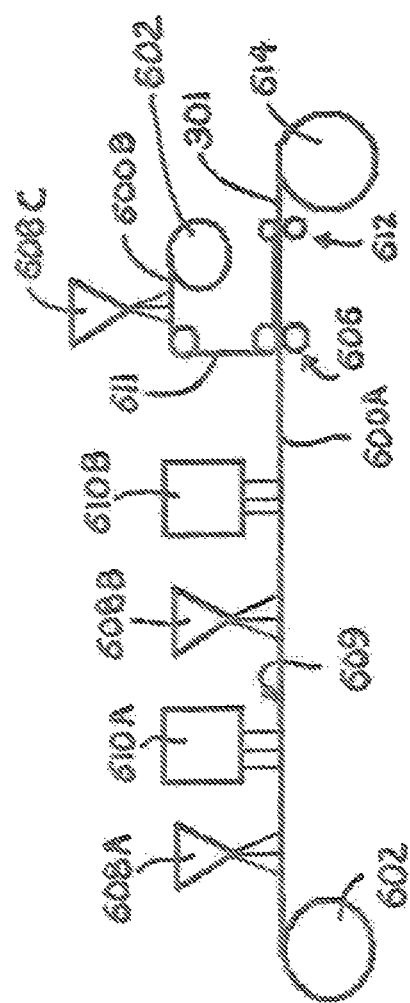
FIG. 8 is a schematic showing one embodiment of the manufacture of a laminate with layer-by-layer bonding.

Referring now to FIG. 8, shown is one embodiment of how the liner 301 may be manufactured. Shown is a simple lamination process in which various health-benefit agents (particles with ranges from nanometers to micrometers) can be stabilized and bonded between substrates 600A and 600B with the pressure sensitive hot-melt adhesive.

Liner materials can be converted into a liner 301 to be later used in the process of making absorbent articles that incorporate liner 301. Absorbent products are made with the liner 301 at a relatively high speed and without altering the machinery in the production line. In other words, the web of liner 301 is converted into an absorbent article liner without having to construct the liner 301 in line during the absorbent article manufacturing process. This is only one example of how the liner 301 may be manufactured and is intended to be non-limiting.

FIG. 8 shows one example of a layer-by-layer bonding process wherein there are two substrates 600A and 600B (e.g. nonwoven or film) coming off of spools 602 and joined at a nip roll 606. Prior to joining the layers at the nip, a layer of adhesive is meltblown with the application unit 608A at about a 45 to 85 degree angle with respect to the substrate surface 609. After the adhesive is applied to the substrate, a Christy feeder 610A applies a health-benefit agent to the substrate 600A. A second Christy feeder 610B applies another layer of health-benefit agent. After the nip roller 606 joins the layers of the materials, the liner 301 is optionally apertured at an aperture unit 612 to allow the health-benefit agent to flow to the wearer's body, and to allow moisture to flow into and through liner 301. SB and SMS may not require apertures because the material may have a high degree of porosity. The resulting laminate may use 3% to about 10% adhesive for high bonding efficiency. The liner 301 may be spooled onto a roll 614 for later conversion.

Figure 9:
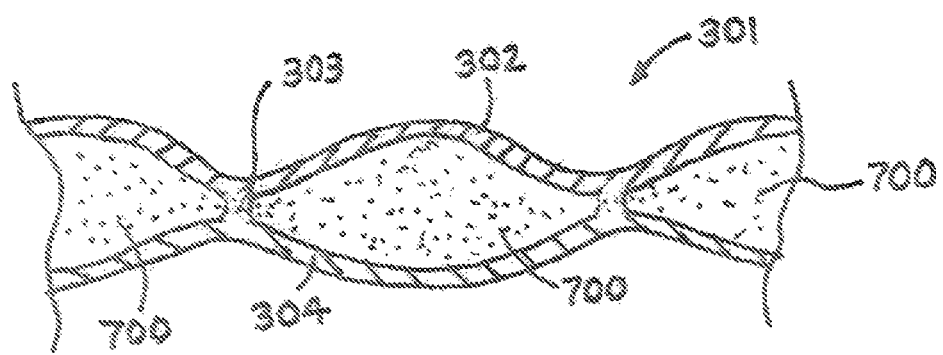
FIG. 9 is a cross-section of one embodiment of the present invention showing the laminate having pockets of health benefit agents.
Figure 10:
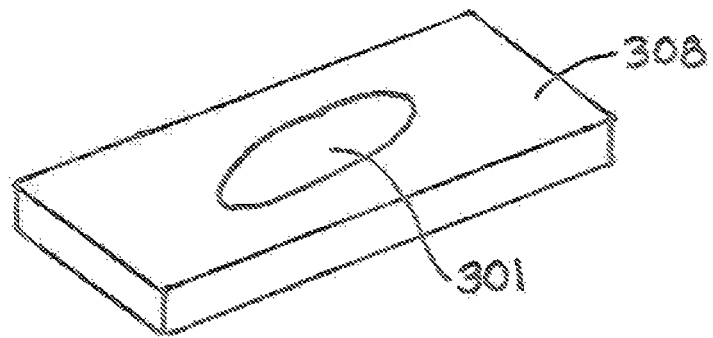
FIG. 10 is a cross-sectional view of another embodiment of a laminate of the present invention having five layers and illustrating liquid transfer through layers.

Another embodiment of the present invention is shown in FIG. 9. Here, a health-benefit agent may be zoned and bonded or attached to a structure such as an absorbent core. For example, the present invention may be directed to a flexible laminate structure that contains continuous and discontinuous areas formed by fusing at least two substrates together. This is done by bonding the substrate(s) at intervals. The bonding methods used for the liner can use adhesive such as the adhesive 303 (shown), and/or thermal, ultrasonic and printing technologies. The resulting pockets 700 contain discrete regions of a functional material, such as particles (e.g. superabsorbent materials and filtration materials, as disclosed herein). As a result of the present invention, it has been discovered that relatively inflexible functional materials may be incorporated within the laminate structure without substantially impairing the flexibility of the structure. For example, in some embodiments, the pockets 700 can be formed to have relatively small dimensions to enhance the flexibility of the liner 301. Moreover, the thickness of the substrate 302 and 304 and the like, can be varied to provide flexibility to the resulting liner 301. While this embodiment is shown in two dimensions, the cross-section of the unseen plane would be the same or similar in appearance.

Figure 12:
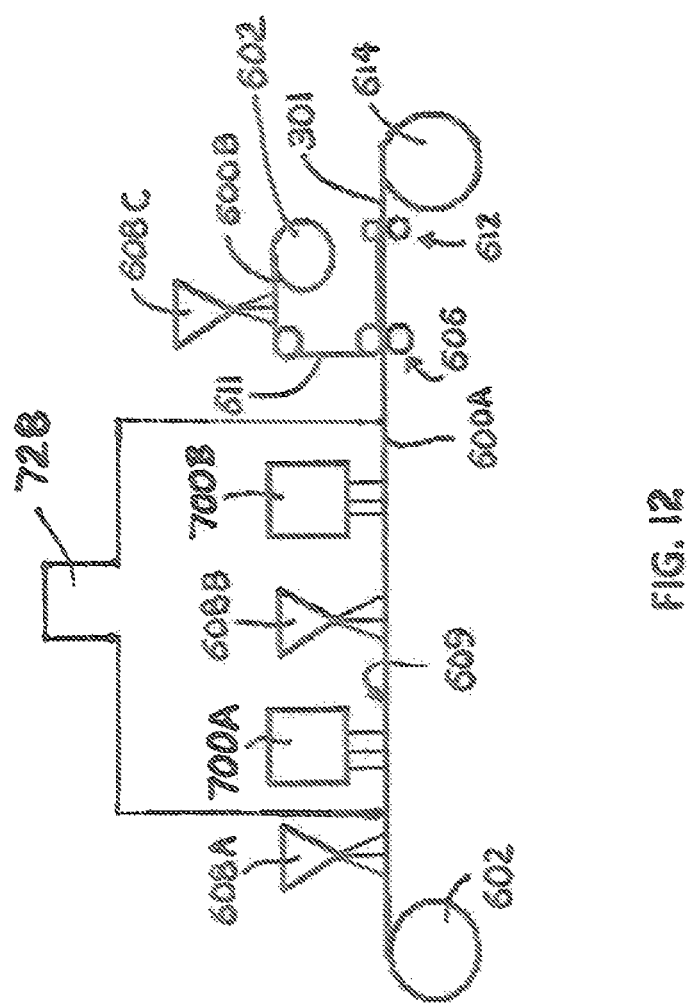
FIG. 12 is a schematic showing another embodiment of the manufacture of a laminate with layer-by-layer bonding.

Referring now to FIG. 12, shown is another embodiment of how a laminate such as liner 301 may be manufactured. Disclosed is a "fine powder" lamination process in which at least one type of health-benefit agent (particulate matter) is stabilized and bonded between substrates 600A and 600B with the pressure-sensitive hot-melt adhesive, the particles having size ranges from several nanometers up to about 120 microns, or from about 10 microns to about 70 microns, or from about 10 microns to about 50 microns, or from about 10 microns to about 30 microns. For certain particulate matter, e.g. encapsulated menthol, the average size of the particles is most desirably 20 microns. Other materials may have an average particle size of 30 microns, or 40 microns, or 50 microns or even up to about 90 microns.

When it is desirable to use particulate matter having an average size of less than 120 microns in a laminate, certain challenges arise. First, when such small particulate matter is applied to a substrate using a screw-feeder such as a Christy feeder, the particulate matter tends to be distributed onto the substrate surface in clumps. To prevent clumping, an electrostatic gun is employed instead of a Christy feeder.

Electrostatic coating is often used in the manufacture of coated metal objects. In that particular application, a basis weight of about 2 grams per square meter (gsm) of powdered material is applied to a metal surface that has been heated. The application is made with an electrostatic gun that imparts a positive electric charge on the particulate matter so that it sticks to the metal. This electric charge lasts several seconds, long enough to keep the particulate matter adhered to the metal surface until the particulate matter is melted thereon, forming crosslinks between the particles. The result is a hard shell-like coating.

There are several differences between the powder coating method for metal and the powder coating method for the substrates of the present disclosure. For instance, the laminate of the present disclosure is not heated and the particulate matter is not melted. There are no crosslinks formed between the substrate or adhesive and the particulate matter, or among the particles. The charge density and retention time of the particulate matter is less. For example, the static charge between the particulate matter and substrate lasts for up to about 2 seconds. Furthermore, the basis weight of particulate matter may be more than thirty times greater (for example, 60 gsm). These differences create a challenge when applying particulate matter to a substrate using an electrostatic gun.

A very general method for constructing a nonwoven laminate of the disclosure includes the steps of making a base by (1) conveying a first substrate and a second substrate, each having an inner surface and an outer surface, (2) attaching a first adhesive layer to the inner surface of the first substrate, and (3) attaching a first layer of the particulate matter to the first adhesive layer. A cover is made by attaching a second adhesive layer to the inner surface of the second substrate. The base is attached to the cover so that the outer surfaces of the first substrate and the second substrate are exposed. Additional layers of adhesive and particulate matter may be disposed between the base and the cover.

Referring to FIG. 12, shown is a schematic of an exemplary apparatus where the above-noted steps may be carried out. The apparatus enables a layer-by-layer bonding process wherein two substrates, 600A and 600B (e.g. nonwoven or film), having layers or health-benefit agent and adhesive there between, are joined together at nip roll 606.

The substrates 600A and 600B are conveyed at identical rates. The machine speeds are influenced by the scale of the manufacturing process and may be about 30 to about 600 meters/min.

An adhesive application unit 608A is aimed in the cross-machine direction at about a 45 to 90 degree angle with respect to the substrate surface 609. Using adhesive application unit 608A, a layer of adhesive is meltblown or otherwise applied to the moving substrate 600A. Likewise, an adhesive layer application unit 608C is aimed with respect to the machine direction at about a 45 to 90 degree angle with respect to the substrate surface 611. Using application unit 608C, a layer of adhesive is meltblown or otherwise applied to the moving substrate 600B.

Figure 13:
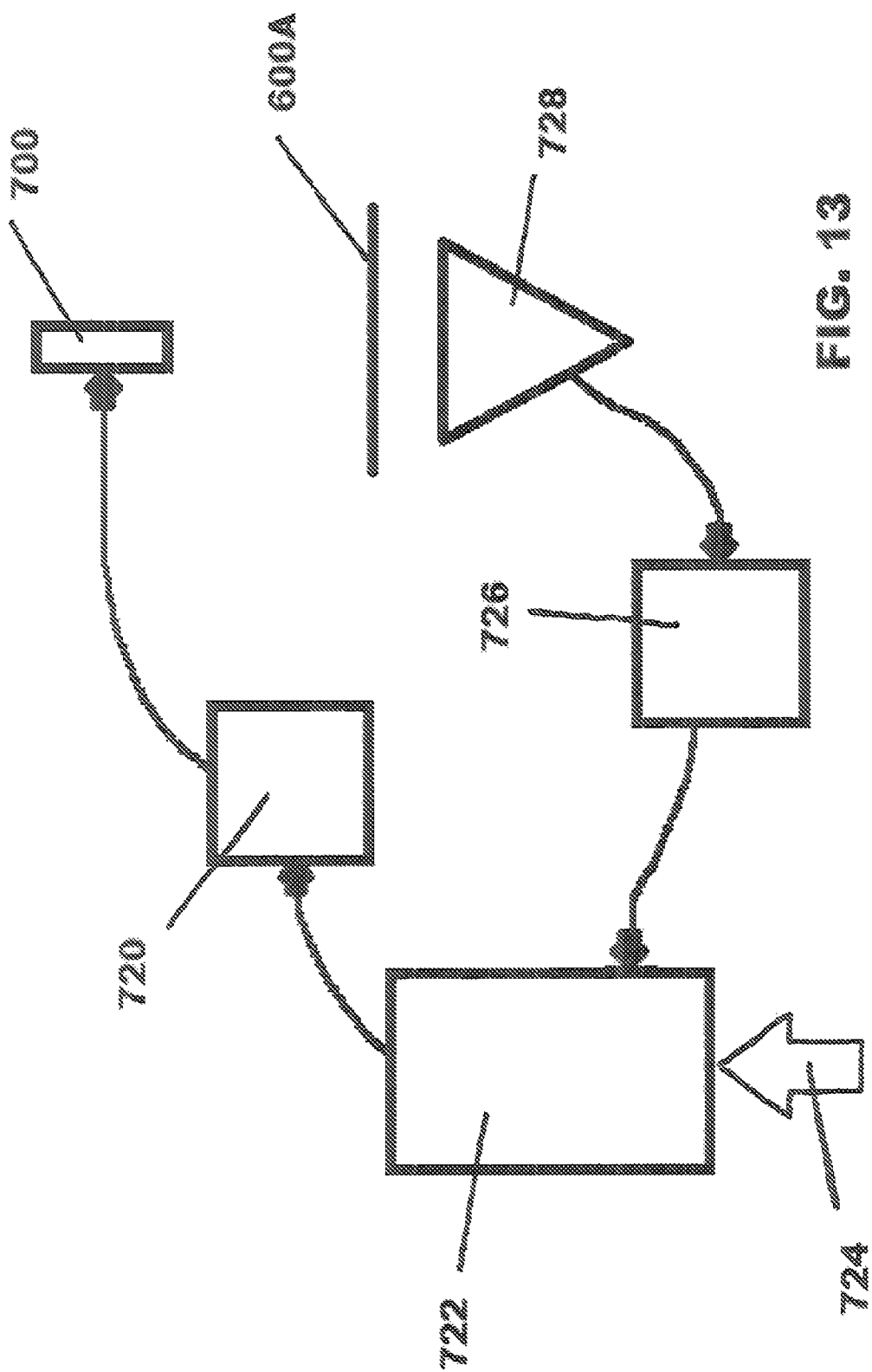
FIG. 13 is a schematic showing one embodiment of an electrostatic particle application system.

The particulate matter is applied to the adhesive layer. To begin, the particulate matter is first "fluidized" by pumping it into a chamber into which air is circulating, thereby suspending the particles in air. Referring to FIG. 13, the particulate matter is fluidized in a feed hopper 722 into which compressed air 724 flows. The particulate matter is pumped into the feed hopper 722 from two sources: a supply hopper (not shown) and a reclaim hopper 728. A feed pump 720 supplies the fluidized particulate matter to the electrostatic gun 700. (One example of a pump that may be used is a PRODIGY II HDLV pump available from the Nordson Corporation of Ohio.)

Electrostatic gun 700A applies the fluidized particulate matter onto the adhesive layer so that the particulate matter becomes attached to substrate 600A by a temporary static charge (until it passes through the nip roll 606) and/or by the adhesive. (Electrostatic guns are available in many different capacities; one example is a PRODIGY II powder coating gun available from the Nordson Corporation of Ohio). Referring to FIG. 12, the electrostatic gun 700A is positioned with respect to the substrate 600A such that it can apply a uniform layer of the particulate matter thereon. In one aspect of the disclosure, electrostatic gun 700A is positioned at an angle of about 90 degrees relative to the surface of substrate 600A, and has a single slot tip.

Referring to FIG. 13, any excess particulate matter that does not adhere to the adhesive layer is collected into the reclaim hopper 728 and fed into the feed hopper 722 using a reclaim pump 726. In one aspect of the disclosure the reclaim system is a down-draft system. The reclaim pump 726 is attached to a containment booth (not shown) that surrounds at least the electrostatic gun(s) 700. One example of a downdraft reclaim system is a HORIZON 100 system, available from Nordson Corporation of Ohio.

A second and optional adhesive application unit 608B is positioned with respect to surface 609 in a manner similar to that of adhesive application unit 608A, and is positioned in series relative to same. Adhesive application unit 608B applies a layer of adhesive onto the layer of particulate matter applied with electrostatic gun 700A, noted above. If the optional second adhesive application unit is utilized, so is a second electrostatic gun, shown at reference 700B.

Electrostatic gun 700B applies yet another layer of health-benefit agent to the adhesive applied by application unit 608B. It is positioned in series relative to electrostatic gun 700A, and otherwise positioned relative the surface 609 in a manner similar to electrostatic gun 608A. Additional layers of adhesive and particulate matter may be added in the same manner. These additional layers allow for a greater total basis weight of particulate matter to be attached to the substrate 600A.

The adhesive side of substrate 600B is joined to the uppermost layer of particulate matter located on substrate 600A. Desirably, pressure is applied to the resulting laminate by passing it through nip roller 606. The time that elapses between the application of the last layer of particulate matter and the joiner at the nip roll 606 is approximately 1-2 seconds. The nip roller 606 applies pressure for better bonding of the laminate elements, thereby creating a more stable laminate. The laminate, which is shown by way of example as liner 301, which are too thick may allow slipping to occur between the first and second nonwoven substrate and/or cause fallout of particulate matter from the edges of the laminate.

As there may be more than one layer of particulate matter, in some aspects of the present disclosure, the first layer of particulate matter has a different chemistry than the second layer of particulate matter. In other aspects, these layers of particulate matter are chemically identical and applied as two layers because the desired amount of particulate matter may be too high to be applied in one layer.

In some aspect of the present disclosure, a layer of particulate matter constitutes 100 percent superabsorbent material. In other aspects the layer of particulate matter contains at least about 95 percent superabsorbent material. The resulting laminate may be desirable for creating absorbent core material for personal care articles such as diapers, bandages and the like.

The examples discussed thus far and in experiments to be discussed are in no way intended to be limiting. For instance, as indicated, there may be more than two substrates and more than one layer of health-benefit agents. The number of layers, either substrate or health-benefit agents, is only limited by the thickness of the laminate that may be determined by the thickness test herein. The thicker the laminate is, the less flexible it becomes. Furthermore, the layers of substrate and health-benefit agents may be diverse materials that may or may not react with respect to one another.

Table 1 describes the different agents and substrates that were tested as described infra. Each structure of laminate/liner 301 is identified by a key code.

TABLE 1

KEY CODE
Lamination with Silica Gel, Xylitol and Superabsorbent

| Key | Code | Health Benefit Composition | Substrate Configuration | Health Benefit Agent % by Wt | Composition Function |
|---|---|---|---|---|---|
| 1 | 091709-1 | Silica Gel | Tissue//SMS | 53 | Dry |
| 2 | 091709-2 | Silica Gel | Tissue//SMS | 67 | Dry |
| 3 | 091709-3 | Silica Gel | Tissue//Tissue | 81 | Dry |
| 4 | 091709-4 | Silica Gel | Tissue//Tissue | 48 | Dry |
| 5 | 091709-5 | Silica Gel | Tissue//Tissue | 32 | Dry |
| 6 | 091709-6 | 80% Silica Gel + 20% Xylitol | Tissue//Tissue | 39 | Dry, anti bacterial |
| 7 | 091709-7 | 80% Silica Gel + 20% Xylitol | Tissue l//Tissue | 39 | Dry, anti bacteria, reducing malodor |
| 8 | 091709-8 | 80% Silica Gel + 20% SAM | Tissue//Tissue | 99 | dry, absorbency |
| 9 | 091709-9 | 80% Silica Gel + 20% SAM | Tissue//Tissue | 31 | dry, absorbency |

Notes:
A. Key 1 & 2 with SMS inner layer may slow fluid intake, which can be overcome with smaller size cut at high-add-on
B. Keys 3, 4, 5 with tissue substrates, will provide quick intake rate at lower cost, can be used as a additional substrate when composition % is relatively low, or cut smaller size and placed in the pad with high add-on of silica gel
C. Keys 6 & 7 will provide dry and anti bacterial functions due to xylitol, it might provide cooling and/or reduction of malodor (See U.S. Pat. No. 6,437,212B1 incorporated herein to the extent is it is consistent.)
D. Keys 8 & 9 with 20% SAM
E. 10-15% of construction Hot melt adhesive 34-5610, One tissue substrate and one SMS substrate.

is optionally pierced by an aperture unit 612. The laminate may be spooled onto a roll 614 for later conversion.

It has been observed that the finer the particulate matter, the more surface area there is to which the adhesive can bond. Thus, the size of the particulate matter is inversely proportional to the amount of adhesive needed to create a satisfactory bond. Desirably, in some aspects of the disclosure, the laminate resulting from this fine powder lamination process may include 5-15 gsm of adhesive for every 20-60 gsm of fine powder.

It is desirable that every separate layer of particulate matter is delivered to a single adhesive layer at a basis weight of about 2 gsm to about 60 gsm; or about 8 gsm to about 40 gsm; or about 10 gsm to about 30 gsm. Layers of particulate matter Test One: The Suppression of *E. coli*

The test objective is to find the highest suppression of colony forming units of *Escherichia coli* as a result of the exposure to prebiotic Oligofructose. For the test, the prebiotic is either located between substrates made with up to two tissues and spunbond-meltblown-spunbond layers. Controls for the health benefit agents were (1) a silica gel only, (2) no health benefit agents, and (3) an adhesive only.

Materials Used:
 Spunbond liner+/−prebiotic treatment (see Table 1)
 Bacterial cultures:
 *Lactobacillus acidophilus* ATCC#314
 *Escherichia coli* ATCC#10789
 Brain Heart Infusion agar plates LAPTg broth (Glucose complete)
LAPTg GD (Glucose depleted or 0.1% glucose)
LAPTg 0.1% glucose; 0.9% oligofructose
Methods of Sample Preparation:

Liners with or without oligofructose were cut into pieces and sterilized with ethylene oxide gas. *Lactobacillus acidophilus* was grown in LAPTg media anaerobically at 37° C. for 48 hours. *Escherichia coli* was grown in LAPTg media and incubated at 37° C. shaking for 24 hours. Culture tubes were set up with a negative control represented by 5 mL LAPTg GD media and a positive control with 5 mL of LAPTg 0.1% glucose and 0.9% oligofructose media. Liners with or without oligofructose were aseptically placed into culture tubes and submerged in 5 mL of LAPTg GD media.

Approximately $2.5 \times 10^6$ colony forming units (CFU) of *Lactobacillus acidophilus* from an overnight culture was added to each of the culture tubes. The tubes were then incubated anaerobically for 6 hours at 37° C. After 6 hours, approximately 250 CFU of *Escherichia coli* overnight culture was added into each of the culture tubes. A 0 hour time count of *Lactobacillus acidophilus* and *Escherichia coli* was determined by serial dilution and plating onto brain heart infusion agar plates.

Culture tubes were incubated anaerobically at 37° C. for 24 hours. The culture tubes were sonicated for one minute five times with a rest period of one minute between sonications. Serial dilutions were made from each culture tube and plated onto brain heart infusion agar plates. The agar plates were then incubated anaerobically at 37° C. for 48 hours. Number of viable *Lactobacillus acidophilus* and *Escherichia coli* was calculated and reported as CFU/ml. In addition the ratio of *Lactobacillus acidophilus* to *Escherichia coli* was calculated by dividing the CFU/ml of *Lactobacillus acidophilus* by the CFU/ml of *Escherichia coli*. Identification of bacteria was based on colony morphology.
Results:

Sample codes are shown in Table 2 below. The sample codes identify the treatment of differing laminate constructions. Table 2 shows that the sample code 111109-4 is superior to the other treatments and laminate construction. In particular, the sample having 27.7 grams of oligofructose per square meter of Liner T/SMS has the highest ratio of *Lactobacillus acidophilus* (La) to *Escherichia coli* (Ec).

TABLE 2

Sample Codes for Different Laminate Construction and Treatment

| Sample Code | Treatment | Ratio La/Ec |
|---|---|---|
| N/A | Media alone | 0.06 |
| N/A | Media +OF | 2.00 |
| 111209-2 | Untreated Liner T/T | 0.50 |
| 111190-5 | 46.3 gsm OF Liner T/T | 3.64 |
| 091709-4 | Silica Control T/T | 0.14 |
| 111209-4 | Untreated liner T/SMS | 0.49 |
| 111109-4 | 27.7 gsm OF Liner T/SMS | 4.44 |
| 030410-1 | 17.7 g gsm OF Liner T/SMS | 3.28 |
| 030410-2 | 9.8 gsm OF Liner T/SMS | 3.78 |
| 030410-5 | 3.2 gsm OF Liner T/SMS | 0.44 |
| 030410-14 | Silica Control T/SMS | 0.04 |
| 030410-9 | Blank T/SMS | 0.02 |
| 030410-13 | Adhesive T/SMS | 0.03 |

(La = *Lactobacillus acidophilus*, Ec = *Escherichia coli*)

TEST Two: Maximum Water Absorption at 37 C and 80% Relative Humidity

The objective of this test is to determine the moisture absorption of different laminate construction with different add-on materials such as silica, xylitol, and superabsorbent material ("SAM"). Controls were (1) no add-on to a tissue and (2) a tissue to tissue or tissue to SMS construction with or without silica add-on. "Add-on" refers to a health benefit agent. The test results are shown in Table 3 located below:

TABLE 3*

| Sample | max water absorption (g) | add-on g/m² | g add-on/sample | water/sample | water/g add-on |
|---|---|---|---|---|---|
| Control | 0.014 | 0 | 0.000 | 0.000 | 0.000 |
| 091709-1A | 0.015 | 53 | 0.273 | 0.000 | 0.001 |
| 091709-1B | 0.014 | 53 | 0.273 | 0.000 | −0.001 |
| 091709-2 | 0.023 | 67 | 0.346 | 0.009 | 0.026 |
| 091709-3 | 0.047 | 81 | 0.418 | 0.033 | 0.078 |
| 091709-4 | 0.038 | 48 | 0.248 | 0.024 | 0.096 |
| 091709-5 | 0.024 | 32 | 0.165 | 0.010 | 0.059 |
| 091709-6 | 0.021 | 39 | 0.201 | 0.007 | 0.035 |
| 091709-7 | 0.024 | 39 | 0.201 | 0.010 | 0.050 |
| 091709-8 | 0.129 | 99 | 0.511 | 0.114 | 0.224 |
| 091709-9 | 0.050 | 31 | 0.160 | 0.036 | 0.223 |
| Silica | 0.007 | 0.1 | 0.112 | 0.007 | 0.063 |

Absorption per gram of add-on
a. Sample size = 2" × 4" = .00516 m²
b. Silica alone picked up on average ~0.065 g water per g add-on
c. Silica/Xylitol picked up ~0.048 g water per g add-on (80% silica)
d. Silica/SAM picked up ~0.224 g water per g add-on
*(See Table 1 for codes.)

Test results show that the sample containing 99 gm² of 80% silica and 20% SAM exhibited the highest moisture absorption at 37 C and 80% relative humidity.

TEST Three: Powder Coating Observations

Tests were performed to determine parameters needed for uniform and adequate bonding of certain substrates and an encapsulated menthol powder. The results of the tests are shown in Table 4, below. The specimens tested were prepared as follows:

1. Each 400-500 foot length of each sample of laminate, labeled Code A-J, was manufactured using two electrostatic guns (to create two layers of powder) at a speed of 140-200 feet/min using the apparatus of FIG. 12 and the corresponding method described herein. An additional parameter for manufacturing the samples is that the menthol powder was supplied to the substrate at 500-1000 g/min using a pinch-valve powder pump having a 600 lbs/hr capacity. Each powder gun had a capacity of 5 cfm and was associated with an individual pump having a capacity of 7 cfm.

2. The substrate was either spunbond (S) or spunbond-meltblown-spunbond (SMS), as indicated below. The spunbond and spunbond-meltblown-spunbond is available from Kimberly-Clark Corporation, and was of the type typically used in the construction of K-C personal care products (e.g. diapers).

3. The particulate matter consisted of encapsulated menthol, available as MULTISAL Menthol Encapsulate, from Salvona Technologies, Inc. of New Jersey.

4. The adhesive used in the laminate was a hot-melt adhesive available as #34-901B from National Starch, Bridgewater, N.J.

TABLE 4

| Code | Substrate | Adhesive (gsm) | MME (gsm) | Powder set % | Speed (Ft/min) | Left Edge/Right edge | Observation |
|---|---|---|---|---|---|---|---|
| A | S/S | 10 | 8 | 15% | 200 | 46/44 | Uniform bond; Bond is Good |
| B | S/S | 10 | 11 | 25 | 200 | 52.4/53.5 | Uniform bond; Bond is Good |
| C | S/S | 10 | 20 | 50 | 200 | 66.5/64.4 | Uniform bond; Bond is Good |
| D | S/S | 10 | 28 | 75 | 200 | 74.2/69.4 | Uniform bond; Bond is Good |
| E | S/S | 15 | 40 | 75 | 150 | 83.5/88.3 | Uniform bond; Bond is Fair |
| F | SMS/SMS | 15 | 40 | 75 | 140 | | Uniform bond; Bond is Fair |
| G | SMS/SMS | 10 | 20 | 75 | 200 | | Uniform bond; Bond is Good |
| H | SMS/SMS | 12 | 30 | 75 | 170 | | Uniform bond; Bond is Good |
| I | | 12 | 30 | 75 | 170 | | Uniform bond; Bond is Good |
| J | | 12 | 30 | 75 | 170 | | Uniform bond; Bond is Good |

The data of Table 4 shows that the variability of the thickness of the layer of particulate matter was 5% or less, as measured at a left-edge location and a right-edge location that is laterally positioned with respect to the left-edge location. This is considered a "uniform" bond.

The definition of a "good" bond is that during normal handling, there is less fall-out of less than 1% by weight of particulate matter is emitted from all edges of the laminate combined. "Normal handling" is generally the type of stress that the laminate, when used as a backsheet of an absorbent product such as a diaper or feminine pad, will experience in the manufacture of and life the absorbent product. A definition of a "fair" bond is that during normal handling, 1% to 2% by weight of particulate matter is emitted from all edges of the laminate combined. The definition of a poor bond is that during normal handling more than 2% by weight of particulate matter is emitted from all edges of the laminate combined. As can be seen, in this particular example, basis weights of 40 gsm produced only a fair bond between the S/S and SMS/SMS substrates.

Test Methods
Co-Culture Assay

*Lactobacillus acidophilus* (ATTC #314) (ATTC, Manassas, Va.) (La) was grown in 20 ml of LAPTg broth (15 g/liter peptone, 10 g/liter tryptone, 10 g/liter glucose, 10 g/liter yeast extract, 1 ml/liter Tween 80, pH to 6.5 and autoclave) for 48 hours anaerobically at 37° C. *Escherichia coli* (ATTC #10789) (ATTC, Manassas, Va.) (Ec) was grown in 20 ml of LAPTg broth overnight at 37° C. shaking. Oligofructose-treated and control liners were cut into 75 cm² strips, placed into individual autoclave pouches (Cardinal Health, McGraw, Ill.), and sterilized with ethylene oxide gas using an Anprolene gas sterilizer (Haw River, N.C.). Untreated control, silica control, and oligofructose liners were aseptically placed into separate culture tubes (BD) to which five ml of LAPTg GD media (15 g/liter peptone, 10 g/liter tryptone, 1 g/liter glucose, 10 g/liter yeast extract, 1 ml/liter Tween 80, pH to 6.5 and autoclave) was added. A negative control culture tube had 5 ml of LAPTg GD media, and a positive control culture tube had five ml of LAPTg 0.1% glucose 0.9% oligofructose (BENEO-Orafti Inc., Teinen, Belgium) in liquid mediaThe optical density (OD) at 540 nm of the La culture was determined using the Spectromax Plus 348 spectrophotometer (Molecular Devices, Sunnyvale, Calif.), and the culture was centrifuged at 5,000 rpm for five minutes in the Avanti J-25I floor centrifuge (Beckman, Fullerton, Calif.). The supernatant was discarded, and 3-6 ml of LAPTg GD was added. A new $OD_{540}$ was taken and the culture was adjusted to an $OD_{540}$ of 1.3-1.5. Two-hundred and fifty of the La culture was added to each of the culture tubes before tubes were incubated anaerobically at 37° C. for 6 hours.

From tube one, the number of La at time 0 was determined using standard dilution and plate count assays. The $OD_{600}$ of the Ec culture was determined, and the culture was diluted into PBS (BD) to a final concentration of $10^{-5}$. 0.25 l of this culture was added to each culture tube and plated on BHI to obtain a 0hr count of Ec. Tubes were incubated anaerobically at 37° C. for 24 hours.

After 24 hours, the tubes were sonicated five times (Branson ultrasonic cleaner 35100, Danbury, Conn.) for one minute with a minute rest time in-between. The cultures were serially diluted, plated in duplicate on BHI agar plates and incubated anaerobically for 48 hours at 37° C. Differentiation between La and Ec was based on colony morphology. Ec appears as yellowish white colonies and La appears as significantly smaller pin point white colonies.

Standard incubators were used to grow bacteria at 37° C. For this lab bench testing, humidity is not important because the liners are submerged in media throughout the entire assay.

Bacterial counts are determined by serial dilution and plating, a standard method. Bacteria were distinguished based on colony morphology. Bacterial counts are reported as CFU/ml or colony forming units per milliliter, a standard method of reporting bacterial numbers. Zero hour counts are used to verify that the *E. coli* and *Lactobacillus* are at the approximately same amount before the tubes are incubated continuously for 24 hours.

Sonication Test

Culture tubes were placed in test tube racks inside of the sonicator water bath, and sonicated for one minute. After one minute, sonication stopped, while tubes stayed in the water bath for one minute. This was repeated until tubes were sonicated for five times. Sonicator used: Branson ultrasonic cleaner 35100, Danbury, Conn.

Particle Size Test

A stack of sieves are used to determine the particle size distribution of a given sample. Thus, for example, a particle that is retained on a sieve with 710 micron openings is considered to have a particle size greater than 710 microns. A particle that passes through a sieve having 710 micron openings and is retained on a sieve having 500 micron openings is considered to have a particle size between 500 and 710 microns. Further, a particle that passes through a sieve having 500 micron openings is considered to have a particle size less than 500 microns, and so on.

The sieves are placed in order of the size of the openings with the largest openings on the top of the stack and the smallest openings on the bottom of the stack. Thus, all of the stimulation material associated with a signal composite can be weighed and placed into the sieve with the largest openings. Alternatively, if it is desired to determine the particle size or particle size distribution of the stimulation material in only a particular portion of the signal composite, only the stimulation material associated with that portion can be weighed and placed into the sieve with the largest openings. U.S. Standard sieves can be used in the sieve stack, including 20 mesh (850 microns), 25 mesh (710 microns), 35 mesh (500 microns), 50 mesh (300 microns) and 170 mesh (90 microns).

The sieve stack is shaken for 10 minutes with a Ro-Tap mechanical Sieve Shaker, Model RX29 available from W. S. Tyler of Mentor, Ohio, or other similar shaking device at standard test conditions. After shaking is complete, the stimulation material retained on each sieve is removed and the weight is measured and recorded. The percentage of particles retained on each sieve is calculated by dividing the weights of the particles retained on each sieve by the initial sample weight.

For particles that are too small for the test method described above, particle size may be measured using SEM (scattered electron microscope) technologies. Specifically, loose particles of about 20 nanometers can be measured for size using laser light scattering. The size of particles incorporated into a polymer or the like may be imaged by SEM or more desirably, by field emission SEM (FE-SEM). The method used (either SEM or FE-SEM) and the resulting images of very small particles can be influenced by particle composition, size, and immediate surroundings such as an adhesive described herein.

Basis Weight (gsm) Test

The "Basis Weight" test is used to determine the mass of cellulosic or synthetic fibers per unit area of tissue or nonwoven sheet. The basis weight can be measured in As-Is (no conditioning), Conditioned (equilibrated to laboratory conditions of 23+/−3.0° C. and 50+/−5% relative humidity) or Bone Dry (oven dried at 105+/−2.0° C. for 25 minutes for a sample weight less than 10.0 grams and a minimum of 8 hours for a sample weighing more than 10 grams). To carry out the test, 16 sheets are stacked and cut to a dimension of 76.2× 76.2+/−1 mm using a die cutter capable of cutting the specimen to the specified dimensions such as a Hudson Machinery part number SE-25 or equivalent with an appropriately designed die. Weigh the cut specimen in grams for as-is, conditioned or bone dry basis weight after appropriate conditions of previously mentioned preparations are completed. If bone dry basis weight is required, the oven dried sample is placed into an air-tight can after drying to prevent moisture from penetrating the sample—the weight of the can is then removed from the calculation of the sample weight. This weight in grams is then multiplied by 6.3492 to report the finished product basis weight in pounds per ream or multiply the sample weight in grams by 10.764 to report the finished product basis weight in grams per square meter (gsm).

Thickness Test

Figure 4:
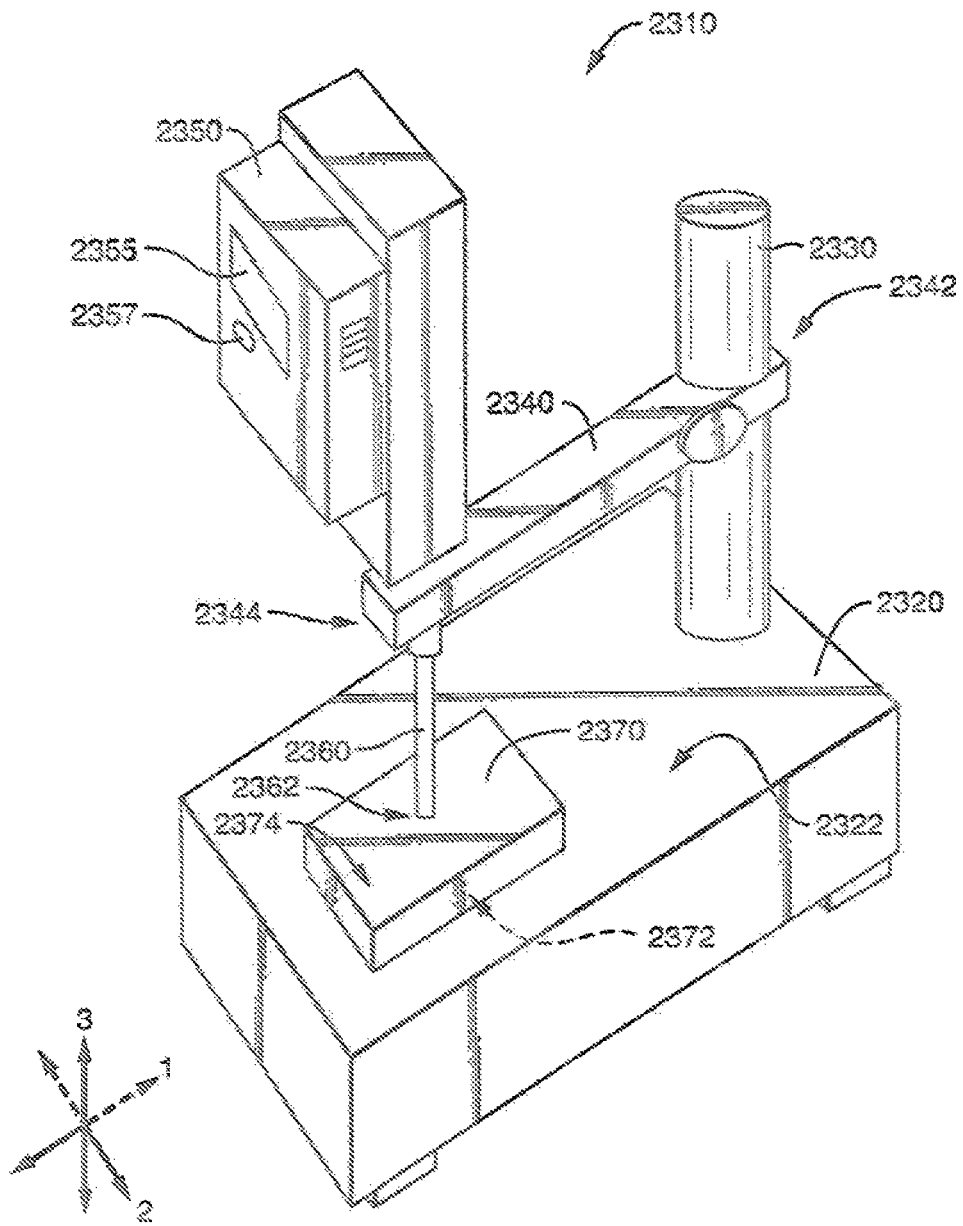
FIG. 4 is a device for measuring the thickness, of the liner of the present invention.

The thickness value of a selected portion or section of an article is determined using a thickness tester such as seen in FIG. 4. The thickness tester 2310 includes a granite base 2320 having a clamp shaft 2330 where the top surface 2322 of the granite base 2320 is flat and smooth. A suitable granite base is a Starret Granite Base, model 653G (available from The L.S. Starrett Company, having a place of business located in Athol, Mass., U.S.A.) or equivalent. A clamp arm 2340 is secured to the clamp shaft 2330 at one end 2342 of the clamp arm 2340, and a digital indicator 2350 is secured to the clamp arm 2340 at the opposing end 2344. A suitable indicator is a Mitutoyo ID-H Series 543 Digimatic Indicator (available from Mitutoyo America Corp., having a place of business located in Aurora, Ill., U.S.A.) or equivalent. Extending downward from the indicator 2350 is a vertically-movable plunger 2360.

To perform the procedure, a block 2370 having a length of 50 mm and a width of 44 mm is placed onto the granite base 2320. The block 2370 is constructed of acrylic and is flat and smooth on at least the bottom surface 2372. The thickness and weight of the block 2370 is configured such that the thickness tester 2310 provides a pressure to the sample of 0.69 kPa (0.1 psi). Next, the thickness tester 2310 is gently lowered such that the bottom surface 2362 of the plunger 2360 is in direct contact with the top surface 2374 of the block 2370 at the longitudinal 1 and transverse 2 center of the block 2370, and the plunger length is shortened by about 50%. The digital indicator 2350 is then tared (or zeroed) by pressing the "zero" button 2357. The digital display 2355 of the digital indicator 2350 should display "0.00 mm" or equivalent. The thickness tester 2310 is then raised and the block 2370 is removed. The test sample is then placed onto the top surface 2322 of the granite base 2320 and the block 2370 is gently placed on top of the test sample such that the block 2370 is substantially centered longitudinally 1 and transversely 2 on the sample. The thickness tester 2310 is then gently lowered again onto the block 2370 such that the bottom surface 2362 of the plunger 2360 is in direct contact with the top surface 2374 of the block 2370 at the longitudinal 1 and transverse 2 center of the block 2370, and the plunger length is shortened by about 50%, to provide a pressure of 0.69 kPa (0.1 psi). After 3 seconds, the measurement from the digital display 2355 is recorded to the nearest 0.01 mm.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

The invention claimed is:

1. A method for constructing a laminate comprising the steps of:
   fluidizing an amount of particulate matter, wherein the particulate matter is selected from the group consisting of menthol, activated charcoal, carbon, xylitol, clay, desiccants, prebiotics, probiotics, surfactants, anti-oxidants, disinfectants, antibacterial agents, antiviral agents, pharmaceutical actives, perfumes, deodorants, opacifiers, astringents, preservatives, and a combination thereof;
   creating a base by
      conveying at a speed of 30 to 600 meters/minute a first substrate and a second substrate, each having an inner surface and an outer surface;
      attaching a first adhesive layer to the inner surface of the first substrate; and applying an amount of the fluidized particulate matter onto the first adhesive layer;

attaching a second adhesive layer to the first layer of particulate matter;

applying additional fluidized particulate matter onto the second adhesive layer to create a second layer of particulate matter, wherein the additional fluidized particulate matter is selected from the group consisting of menthol, activated charcoal, carbon, xylitol, clay, desiccants, prebiotics, probiotics, surfactants, anti-oxidants, disinfectants, antibacterial agents, antiviral agents, pharmaceutical actives, perfumes, deodorants, opacifiers, astringents, preservatives, and a combination thereof, wherein the first layer of particulate matter is chemically different than the second layer of particulate matter, and wherein at least one of:
  (i) the first layer of particulate matter consists of the fluidized particulate matter and the first adhesive layer, and
  (ii) the second layer of particulate matter consists of the additional fluidized particulate matter and the second adhesive layer;

creating a cover by attaching a third adhesive layer to the inner surface of the second substrate; and attaching the base to the cover so that the outer surfaces of the first substrate and the second substrate are exposed.

2. The method of claim 1 wherein the steps of conveying a first substrate and a second substrate, each having an inner surface and an outer surface; attaching a first adhesive layer to the inner surface of the first substrate; and applying an amount of the fluidized particulate matter onto the first adhesive layer to create a first layer of particulate matter are performed in sequential order.

3. The method of claim 1 wherein 8 gsm to 30 gsm of the particulate matter is attached to the first adhesive layer.

4. The method of claim 1 wherein the laminate is constructed at an ambient temperature.

5. The method of claim 1 wherein the other of the at least one of the first layer of particulate matter and the second layer of particulate matter further comprises superabsorbent material.

6. The method of claim 1 wherein the particulate matter is 10 microns to 50 microns in size.

7. The method of claim 1 wherein the particulate matter is 10 microns to 30 microns in size.

8. The method of claim 1 wherein creating a cover by attaching a third adhesive layer to the inner surface of the second substrate includes applying adhesive directly to the inner surface of the second substrate prior to attaching the base to the cover so that the outer surfaces of the first substrate and the second substrate are exposed.

9. The method of claim 1, wherein 8 gsm to 40 gsm of the particulate matter is applied onto the first adhesive layer with an electrostatic gun to create the first layer of particulate matter, the particulate matter of the first layer being between 2 microns to 120 microns in size.

* * * * *